US006326395B1

(12) United States Patent
Tidwell et al.

(10) Patent No.: US 6,326,395 B1
(45) Date of Patent: Dec. 4, 2001

(54) ANTIFUNGAL ACTIVITY OF DICATIONIC MOLECULES

(75) Inventors: Richard R. Tidwell, Pittsboro, NC (US); David W. Boykin, Atlanta, GA (US); John R. Perfect, Durham, NC (US)

(73) Assignees: Duke University, Durham, NC (US); University of North Carolina-Chapel Hill, Chapel Hill, NC (US); Georgia State University Research Found, Inc., Atlanta, GA (US)

( * ) Notice: Subject to any disclaimer, the term of this patent is extended or adjusted under 35 U.S.C. 154(b) by 0 days.

(21) Appl. No.: 09/396,836

(22) Filed: Sep. 15, 1999

Related U.S. Application Data

(60) Provisional application No. 60/100,928, filed on Sep. 17, 1998.

(51) Int. Cl.[7] .................. A61K 31/34; C07D 321/00; C07D 307/00

(52) U.S. Cl. ................ 514/461; 549/200; 549/210

(58) Field of Search ................ 514/461; 549/200

(56) References Cited

U.S. PATENT DOCUMENTS

| | | | |
|---|---|---|---|
| 4,034,010 | 7/1977 | Hamano et al. | 260/564 |
| 4,324,794 | 4/1982 | Tidwell et al. | 424/273 B |
| 4,397,863 | 8/1983 | Tidwell et al. | 424/274 |
| 4,619,942 | 10/1986 | Tidwell et al. | 514/415 |
| 4,933,347 | 6/1990 | Tidwell et al. | 514/256 |
| 4,940,723 | 7/1990 | Tidwell et al. | 514/396 |
| 4,963,589 | 10/1990 | Tidwell et al. | 514/636 |
| 5,202,320 | 4/1993 | Tidwell et al. | 514/218 |
| 5,206,236 | 4/1993 | Tidwell et al. | 514/218 |
| 5,428,051 | 6/1995 | Tidwell et al. | 514/394 |
| 5,521,189 | 5/1996 | Boykin et al. | 514/256 |
| 5,578,631 | 11/1996 | Tidwell et al. | 514/394 |
| 5,594,138 | 1/1997 | Dykstra et al. | 540/596 |
| 5,602,172 | 2/1997 | Boykin et al. | 514/461 |
| 5,606,058 | 2/1997 | Boykin et al. | 544/242 |
| 5,622,955 | 4/1997 | Boykin et al. | 514/256 |
| 5,627,184 | 5/1997 | Boykin et al. | 514/256 |
| 5,639,755 | 6/1997 | Dykstra et al. | 514/256 |
| 5,643,935 | 7/1997 | Dykstra et al. | 514/394 |
| 5,667,975 | 9/1997 | Dykstra et al. | 435/6 |
| 5,668,167 | 9/1997 | Tidwell et al. | 514/411 |
| 5,686,456 | 11/1997 | Boykin et al. | 514/256 |
| 5,723,288 | 3/1998 | Dykstra et al. | 435/6 |
| 5,723,495 | 3/1998 | Hall et al. | 514/633 |

FOREIGN PATENT DOCUMENTS

| | | | |
|---|---|---|---|
| 2833135 | 2/1980 | (DE) | A61K/7/48 |
| 2122208 | 11/1972 | (DE) | C07D/49/38 |
| 51110531A | 9/1976 | (JP) | A61K/31/15 |
| WO 96/40145 | 12/1996 | (WO) | A61K/31/55 |

OTHER PUBLICATIONS

Barchiesi et al.; Effect of pentamidine on the growth of *Cryptococcus neoformans*, Journal of Antimicrobial Chemotherapy (1994) 33, pp. 1229–1232.

Bell et al.; Structure–Activity Relationships of Analogs of Pentamidine against *Plasmodium falciparum* and *Leishmania mexicana amazonensis*, Antimicrobial Agents and Chemotherapy, Jul. 1990, vol. 34, No. 7, p. 1381–1386.

Bell et al.; Structure–Activity Relationships of Pentamidine Analogs against *Giardia lamblia* and Correlation of Antigiardial Activity with DNA–Binding Affinity, Antimicrobial Agents and Chemotherapy, vol. 35, No. 6, Jun. 1991, p. 1099–1107.

Bell et al.; Structure–Activity Studies of Dicationically Substituted Bis–Benzimidazoles against *Giardia lamblia*: Correlation of Antigiardial Activity with DNA–Binding Affinity and Giardial Topoisomerase II Inhibition, Antimicrobial Agents and Chemotherapy, vol. 37, No. 12, Dec. 1993, p. 2668–2673.

Berger et al.; Metabolic N–Hydroxylation of Pentamidine in Vitro, Antimicrobial Agents and Chemotherapy, Sep. 1990, vol. 34, No. 9, pp. 1678–1684.

Boykin et al.; Dicationic Diarylfurans as Anti–*Pneumocystis carinii* Agents, J. Med. Chem., vol. 38, pp. 912–916, (1995).

Cameron et al.; Correlation of In Vitro Fluconazole Resistance of Candida Isolates in Relation to Therapy and Symptoms of Individuals Seropositive for Human Immunodeficiency Virus Type 1, Antimicrobial Agents and Chemotherapy, Nov. 1993, vol. 37, No. 11, p. 2449–2453.

Cory et al.; Structure and DNA Binding Activity of Analogues of 1,5–Bis(4–amidinophenoxy)pentane (Pentamidine), J. Med. Chem., 1992, vol. 35, pp. 431–438.

Donkor et al.; Pentamidine Congeners. 2. 2–Butene–Bridged Aromatic Diamidines and Diimidazolines as Potential Anti–*Pneumocystis carinii* Pneumonia Agents, J. Med. Chem., vol. 37, pp. 4554–4557, (1994).

Isalska et al.; Letters to the Editor, Actinomycosis of the tongue, Journal of Infection (1991) 22, pp. 201–212.

Jones et al.; Novel Pentamidine Analogs in the Treatment of Experimental *Pneumocystis carinii* Pneumonia, Antimicrobial Agents and Chemotherapy, Jun. 1990, vol. 34, No. 6, pp. 1026–1030.

Keku et al.; The in vitro HL–60 cell—*Trypanosoma brucei rhodesiense* culture system: a rapid in vitro drug screen, Tropical Medicine and Parasitology, (1995), vol. 46 No. 4, pp. 256–262.

(List continued on next page.)

*Primary Examiner*—Kevin E. Weddington
(74) *Attorney, Agent, or Firm*—Myers Bigel Sibley & Sajovec

(57) ABSTRACT

Methods of treating fungal infections comprise administering a therapeutically effective amount of a compound described by Formulas [(I)–(VI)]. Examples of fungal infections include *Candida albicans, Cryptococcus neoformans, Aspergillus fumigatus, Fusarium solani,* and combinations thereof.

28 Claims, No Drawings

OTHER PUBLICATIONS

Kumar et al.; Anti–*Pneumocystis carinii* pneumonia activity of dicationic 2,4–diarylpyrimidines, Eur. J. Med. Chem. (1996) 31, pp. 767–773.

Lindsay et al.; Activity of Pentamidine and Pentamidine Analogs against *Toxoplasma gondii* in Cell Cultures, Antimicrobial Agents and Chemotherapy, Sep. 1991, vol. 35, No. 9, pp. 1914–1916.

Pfaller et al.; Variations in Fluconazole Susceptibility and Electrophoretic Karyotype among Oral Isolates of *Candida albicans* from Patients with AIDS and Oral Candidiasis, Journal of Clinical Microbiology, vol. 32, No. 1, Jan. 1994, p. 59–64.

Sahai et al.; Correspondence, Fluconazole resistance in AIDS patients, The Pharmacokinetic Research Unit in Infectious Diseases, The Ottawa General Hospital, Ottawa, Ontario, Canada, undated, pp. 937–939.

Tidwell et al.; Development of Pentamidine Analogues as New Agents for the Treatment of *Pneumocystis carinii* Pneumonia, vol. 616 of the Annals of the New York Academy of Sciences, Dec. 26, 1990, pp. 420–441.

Tidwell et al.; Analogues of 1,5–Bis(4–amidinophenoxy) pentant (Pentamidine) in the Treatment of Experimental *Pneumocystis carinii* Pneumonia, J. Med. Chem., vol. 33, pp. 1252–1257, (1990).

Tidwell et al.; Pentamidine and Related Compounds in the Treatment of *Pneumocystis carinii* Infection, *Pneumocystis carinii* Pneumonia, Second Edition, Revised and Expanded, Copyright 1993 by Marcel Dekker, Inc., pp. 560–583.

Tidwell et al.; Activity of Cationically Substituted Bis–Benzimidazoles against Experimental *Pneumocystis carinii* Pneumonia, Antimicrobial Agents and Chemotherapy, Aug. 1993, vol. 37, No. 8, p. 1713–1716.

*The Pharmacological Basis of Therapeutics*, Goodman and Gilman, 9th Edition, pp. 989 & 1175 (1996).

*Principals of Internal Medicine*, Harrison, 14th Edition, pp. 1161–1162 (1998).

Anne et al.; "Antifungal and Antibacterial Activities of Diarylamidine Derivatives," *Antimicrobial Agents and Chemotherapy* 18:2 231–239 (Aug. 1980).

Boykin et al.; "Anti–Pneumocystis Activity of Bis–Amidoximes and Bis–O–Alkylamidoximes Prodrugs," *Bioorganic & Medicinal Chemistry Letters* 6:24 3017–3020 (1996).

Boykin et al.; "2,5–Bis[4–(N–alkylamidino)phenyl]furans as Anti–*Pneumocystis carinii* Agents," *J. Med. Chem.* 41:1 124–129 (1998).

Das et al.; "Synthesis and Antiprotozoal Activity of 2,5–Bis(4–guanylphenyl)furans," *Journal of Medicinal Chemistry* 20:4 531–536 (1977).

Del Poeta et al.; "In Vitro Antifungal Activities of a Series of Dication–Substituted Carbazoles, Furans, and Benzimidazoles," *Antimicrobial Agents and Chemotherapy* 42:10 2503–2510 (Oct. 1998).

Hildebrandt et al.; "Identification and Characterization of an Endo/exonuclease in *Pneumocystis carinii* that is Inhibited by Dicationic Diarylfurans with Efficacy Against Pneumocystis Pneumonia," *J. Euk. Microbiol.* 45:1 112–121 (1998).

Trent et al.; "Targeting the Minor Groove of DNA: Crystal Structures of Two Complexes between Furn Derivatives of Berenil and the DNA Dodecamer," *J. Med. Chem.* 39:23 4554–4562 (1996).

International Search Report, PCT/US99/21383, Date of Mailing: Aug. 15, 2000.

Berger et al.: "Hydroxylation of Pentamidine by Rat Liver Microsomes," *The Journal of Pharmacology and Experimental Therapeutics* 256:3 883–889 (1991).

Del Poeta et al.: "Structure–in Vitro Activity Relationships of Pentamidine Analogues and Dication–Substituted Bis–Benzimidazoles as New Antifungal Agents," *Antimicrobial Agents and Chemotherapy* 42:10 2495–2502 (Oct. 1998).

Del Poeta et al.: "In–Vitro Activity of Dicationic Aromatic Compounds and Fluconazole Against Cryptococcus Neoformans and Candida SPP," *Journal of Antimicrobial Chemotherapy* 44:2 223–228 (Aug. 1999).

Donkor et al.: "Antimicrobial Activity of Geometric Isomers of Butamidine and Related Compounds," *Pharmaceutical Research* 13:9 S141 (Sep. 1996).

Fairley et al.: "Structure, DNA Minor Groove Binding and Base Pair Specificity of Alkyl– and Aryl–Linked Bis(amidinobenzimidazoles) and Bis(amidinoindoles)," *Journal of Medicinal Chemistry* 36:12 1746–1753 (1993).

Hopkins et al.: "Extended Aromatic Furan Amidino Derivatives as Anti–Pneumocystis Carinii Agents," *Journal of Medicinal Chemistry* 41:20 3872–3878 (1998).

Li et al.: "Design and Analysis of Organic Cations that Inhibit Interactions of the HIV–1 Rev Protein with RRE RNA," *Structure, Motion, Interaction and Expression of Biological Macromolecules* 10:2 137–145 (1998).

St–Germain et al.: "Effects of Pentamidine Alone and in Combination with Ketoconazole or Itraconazole on the Growth of Candida Albicans," *Antimicrobial Agents and Chemotherapy* 34:12 2304–2306 (Dec. 1990).

Tidwell et al.: "Diarylamidine Derivatives With One or Both of the Aryl Moieties Consisting of an Indole or Indole–like Ring. Inhibitors of Arginine–Specific Esteroproteases," *Journal of Medicinal Chemistry* 21:7 613–623 (Jul. 1978).

International Search Report, PCT/US 99/21383; Date of Mailing: Nov. 28, 2000.

ANTIFUNGAL ACTIVITY OF DICATIONIC MOLECULES

CROSS-REFERENCE TO RELATED APPLICATIONS

The instant application claims priority to U.S. Provisional Application Serial No. 60/100,928 filed Sep. 17, 1998, the disclosure of which is incorporated herein by reference in its entirety.

The present invention was made with Government support under Grant Number 5-U19-AI33363 from the National Institutes of Health. The government has certain rights to this invention.

FIELD OF THE INVENTION

The invention generally relates to methods for treating fungal infections.

BACKGROUND OF THE INVENTION

The incidence of fungal infections in the immunocompromised population has significantly increased over the past several years. In particular, Candida species, especially *Candida albicans,* are often significant pathogens in patients infected with human immunodeficinecy virus (HIV). As an example, infections can range from somewhat mild oropharyngeal or vulvovaginal candidiasis to severe debilitating mucocutaneous candidiasis. Moreover, AIDS patients suffering from oral candidiasis may also experience esophageal candidiasis which has been known to lead to gastrointestinal bleeding and perforation. *Candida albicans* is a species which is commonly isolated from patients with the above-mentioned infections.

Treatment of candidiasis has typically involved two classes of drugs: (1) polyenes such as amphotericin B and nystatin; and (2) azoles such as clotrimazole, ketoconozole, fluconozole, and itraconazole. Since immunosuppression in AIDS-infected patients often occurs over an extended period of time, fungal reinfection may be common. Accordingly, these patients commonly receive prolonged antifungal therapy. Widespread antifungal therapy, however, has raised issues regarding the increased level of resistance among isolates of the Candida species, especially with respect to fluconozole. See Pfaller, M. A., et al., *Journal of Clinical Microbiology,* January 1994, pp. 59–64; and Cameron, M. L., et al., *Antimicrobial Agents and Chemotherapy,* November 1993, pp. 2449–2453.

In view of the above, there remains a need in the art to develop new antifungal treatment methods utilizing compounds which address the problems noted above. It would especially be desirable if the use of such compounds displayed increased fungal activity at acceptable dosage levels. Accordingly, it is an object of the present invention to provide new antifungal treatment methods exhibiting increased fungal activity at acceptable dosage levels.

SUMMARY OF THE INVENTION

The above object as well as others is provided by the present invention.

In one aspect, the invention provides a method of combating a fungal infection in a subject in need of such a treatment. The method comprises administering to the subject an effective fungal infection-combating amount of a compound [(I)–(VI)] selected from the group consisting of:

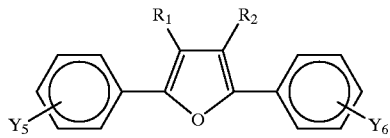

(I)

wherein $R_1$ and $R_2$ may be the same or different and selected from the group consisting of H, loweralkyl, aryl, alkylaryl, aminoalkyl, aminoaryl, halogen, oxyalkyl, oxyaryl, and oxyarylalkyl; and wherein $Y_5$ and $Y_6$ are present in the meta or para positions and may the same or different and are represented by the formula (a) or (b) selected from the group consisting of:

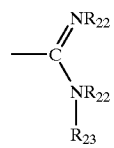

(a)

wherein:

each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; and

(b)

wherein $Y_3$ is selected from the group consisting of NR′′′ and O;

wherein R′′′ is selected from the group consisting of H and loweralkyl;

and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl;

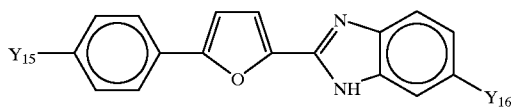
(II)

wherein $Y_{15}$ and $Y_{16}$ may be the same or different and represented by the formula:

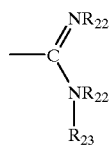

wherein:

each $R_{22}$ is independently selected from the group consisting of H, loweralkyl, alkoxyalkyl, hydroxyalkyl, aminoalkyl, alkylaminoalkyl, alkylamino, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

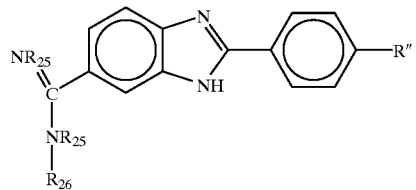
(III)

wherein each $R_{25}$ is independently selected from the group consisting of H, loweralkyl, alkoxyalkyl, hydroxyalkyl, aminoalkyl, alkylaminoalkyl, cycloalkyl, aryl, or alkylaryl or two $R_{25}$ groups together represent substituted or unsubstituted $C_2$–$C_{10}$ alkyl, hydroxyalkyl, or alkylene; and $R_{26}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

R" is hydroxy, alkoxyalkyl, hydroxyalkyl, alkoxyaryl, aryl, or the substituent selected from the formula (i) and (ii) consisting of:

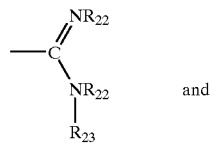
(i)

and

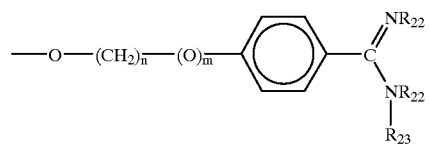
(ii)

wherein:

n and m may be independently selected and each range from 0 to 6; each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

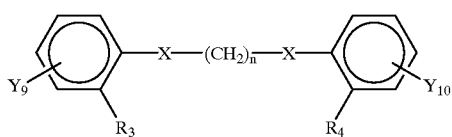
(IV)

wherein:

is from 2 to 6;

X is selected from the group consisting of O, NH, and S;

$Y_9$ and $Y_{10}$ may be in the meta or para position, are independently selected and are each represented by the formula:

wherein each $R_{30}$ is selected from the group consisting of H, hydroxy, loweralkyl, oxyalkyl, alkoxyalkyl, cycloalkyl, aryl, hydroxyalkyl, aminoalkyl, and alkylaminoalkyl; and wherein each of the two $R_{30}$ groups together may represent $C_2$–$C_{10}$ alkyl, hydroxyalkyl, or alkylene;

wherein $R_{31}$ is selected from the group consisting of H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

wherein $R_3$ and $R_4$ may be the same or different and are selected from the group consisting of H, amino nitro, loweralkyl, alkoxyalkyl, hydroxyalkyl, aminoalkyl, alkylaminoalkyl, cycloalkyl, aryl, or alkylaryl;

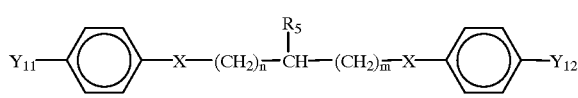
(V)

wherein X may be O, NH, or S; n and m may be the same or different and range from 2 to 6;

wherein $Y_{11}$ and $Y_{12}$ may be the same or different and represented by the formula:

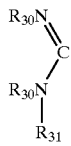

wherein each $R_{30}$ is selected from the group consisting of H, loweralkyl, oxyalkyl, alkoxyalkyl, cycloalkyl, aryl, hydroxyalkyl, aminoalkyl, and alkylaminoalkyl; and wherein each of the two $R_{30}$ groups together may represent represent $C_2$–$C_{10}$ alkyl, hydroxyalkyl, or alkylene;

wherein $R_{31}$ is selected from the group consisting of H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

wherein $R_5$ is selected from the group consisting of H, hydroxy, and

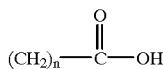

wherein n ranges from 0 to 3;

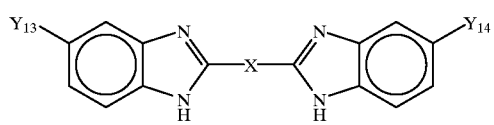
(VI)

wherein X is $C_1$ to $C_{12}$ linear or branched, saturated or unsaturated alkyl containing up to four double bonds, or is substituted or unsubstituted aryl;

wherein $Y_{13}$ and $Y_{14}$ may be the same or different and are represented by the formula:

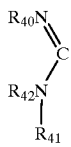

wherein $R_{40}$ and $R_{42}$ are each independently selected from the group consisting of H, loweralkyl, cycloalkyl, substituted aryl, and unsubstituted aryl, or wherein $R_{40}$ and $R_{42}$ together may represent represent $C_2$–$C_{10}$ alkyl, hydroxyalkyl, alkylene, substituted aryl, or unsubstituted aryl; and wherein $R_{41}$ may be H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

In yet another aspect, the invention provides compounds for administering to a subject in need of fungal treatment. The compounds are represented by the formula:

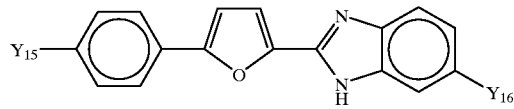

wherein $Y_{15}$ and $Y_{16}$ may be the same or different and represented by the formula:

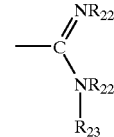

wherein:
each $R_{22}$ is independently selected from the group consisting of H, loweralkyl, alkoxyalkyl, hydroxyalkyl, aminoalkyl, alkylamino, alkylaminoalkyl, cycloalkyl, aryl, or alkylaryl or two $R_{22}$ groups together represent $C_2$–$C_{10}$ alkyl, hydroxyalkyl, or alkylene;

$R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

and pharmaceutically acceptable salts thereof.

Further, the invention provides the above mentioned compounds and salts thereof as pharmaceutical formulations as described in greater detail herein.

The fungal infections that are addressed by the methods of the invention are generally selected from the group consisting of *Candida albicans, Cryptococcus neoformans, Aspergillus fumigatus, Fusarium solani,* and combinations thereof. Also, the methods of the invention may be used in combating Candida species other than *C. albicans* as well as fluconazole-resistant strains of *Candida albicans* and *Cryptococcus neoformans.*

The foregoing and other objects and aspects of the present invention are described in greater detail in the specification set forth hereinbelow.

DETAILED DESCRIPTION OF THE PREFERRED EMBODIMENTS

The present invention now will be described more fully hereinafter with reference to the accompanying specification and examples, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

As used herein, the term "lower alkyl" refers to C1 to C4 linear or branched alkyl, such as methyl, ethyl, propyl, butyl, isopropyl, sec-butyl, and tert-butyl. The term "cycloalkyl" as used herein refers to C3 to C6 cyclic alkyl, such as cyclopropyl, cyclobutyl, cyclopentyl, and cyclohexyl. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —$CH_2OH$, —$(CH_2)_2OH$, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc. The term "oxyalkyl" as used herein refers to C1 to C4 oxygen-substituted alkyl, i.e., —$OCH_3$, and the term "oxyaryl" as used herein refers to C3 to C10 oxygen-substituted cyclic aromatic groups. The term "lower alkoxy" as used herein refers to C1 to C4 linear or branched alkoxy, such as methoxy, ethoxy, propyloxy, butyloxy, isopropyloxy, and t-butyloxy. It should be appreciated that the various groups referred to above may be substituted or unsubstituted with various functional groups known to one skilled in the art.

As noted above, the methods of the present invention are useful for treating antifungal infections attributable to, for example, *Candida albicans, Cryptococcus neoformans, Aspergillus fumigatus, Fusarium solani,* and combinations thereof. The methods of the invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with all weights being calculated based upon the weight of the active based, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intravenous or intramuscular injection. The duration of the treatment is usually once per day for a period of two to three weeks or until the fungal infection is essentially controlled. Lower doses given less frequently can be used to prevent or reduce the incidence of recurrence of the infection.

In accordance with the present method, pharmaceutically active compounds as described herein, or pharmaceutically acceptable salts thereof, may be administered orally as a solid or as a liquid, or may be administered intramuscularly or intravenously as a solution, suspension, or emulsion. Alternatively, the compounds or salts may also be administered by inhalation, intravenously or intramuscularly as a liposomal suspension. When administered through inhalation the active compound or salt should be in the form of a plurality of solid particles or droplets having a particle size from about 0.5 to about 5 microns, preferably from about 1 to about 2 microns.

The present invention also provides a pharmaceutical composition suitable for intravenous or intramuscular injection. The pharmaceutical composition comprises a compound of Formulas (I) through (VI) described herein, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, typically by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula (I) through (VI) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I) through (VI), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

Further, the present invention provides liposomal formulations of the compounds disclosed herein and salts thereof.

The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of a desired compound described herein or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds may be administered via an aerosol suspension of respirable particles in a manner set forth in U.S. Pat. No. 5,628,984, the disclosure of which is incorporated herein by reference in its entirety.

Preferably, when the pharmaceutical formulation suitable for administration as an aerosol is in the form of a liquid, the formulation will comprise a water-soluble compound or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts thereof. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds for use in the methods of the invention include, but are not limited to:

4-(N-cyclopentylamidino)-1,2-phenylene diamine hydrochloride
2,5-Bis[2-(5-amidino)benzimidazoyl]furan hydrochloride
2,5-Bis[2-{5-(2-imidazolino)}benzimidazoyl]furan hydrochloride
2,5-Bis[2-(5-N-isopropylamidino)benzimidazoyl]furan hydrochloride
2,5-Bis[2-(5-N-cyclopentylamidino)benzimidazoyl]furan hydrochloride
2,5-Bis[2-(5-amidino)benzimidazoyl]pyrrole hydrochloride
2,5-Bis[2-{5-(2-imidazolino)}benzimidazoyl]pyrrole hydrochloride
2,5-Bis[2-(5-N-isopropylamidino)benzimidazoyl]pyrrole hydrochloride
2,5-Bis[2-(5-N-cyclopentylamidino)benzimidazoyl]pyrrole hydrochloride
1-Methyl-2,5-Bis[2-(5-amidino)benzimidazoyl]pyrrole hydrochloride
2,5-Bis[2-{5-(2-imidazolino)}benzimidazoyl]-1-methylpyrrole hydrochloride
2,5-Bis[2-(5-N-cyclopentylamidino)benzimidazoyl]1-methylpyrrole hydrochloride
2,5-Bis[2-(5-N-isopropylamidino)benzimidazoyl]thiophene hydrochloride
2,6-Bis[2-{5-(2-imidazolino)}benzimidazoyl]pyridine hydrochloride
2,6-Bis[2-(5-amidino)benzimidazoyl]pyridine hydrochloride
4,4'-Bis[2-(5-N-isopropylamidino)benzimidazoyl]1,2-diphenylethane hydrochloride
4,4'-Bis[2-(5-N-cyclopentylamidino)benzimidazoyl]-2,5-diphenylfuran hydrochloride
2,5-Bis[2-(5-amidino)benzimidazoyl]benzo[b]furan hydrochloride
2,5-Bis[2-(5-N-cyclopentylamidino)benzimidazoyl]benzo[b]furan hydrochloride
2,7-Bis[2-(5-N-isopropylamidino)benzimidazoyl]fluorene hydrochloride
2,5-Bis-[4-(3-(N-morpholinopropyl)carbamoyl)phenyl]furan dihydrochloride
2,5-Bis[4-(2-N,N-dimethylaminoethylcarbamoyl)phenyl]furan dihydrochloride
2 5-Bis[4-(3-N,N-dimethylaminopropylcarbamoyl)phenyl]furan dihydrochloride
2,5-Bis[4-(3-N-methyl-3-N-phenylaminopropylcarbamoyl)phenyl]furan dihydrochloride
2,5-Bis[4-(3-N, $N^8$,$N^{11}$-trimethylaminopropylcarbamoyl)phenyl]furan dihydrochloride
2,5-Bis[3-amidinophenyl]furan dihydrochloride
2,5-Bis-[3-(N-isopropylamidino)amidinophenyl]furan dihydrochloride
2,5-Bis[3[(N-(2-dimethylaminoethyl)amidino]phenylfuran dihydrochloride As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, in solution. After the reaction is complete, the salts are crystallized from solution by the addition of an appropriate amount of solvent in which the salt is insoluble.

Compounds employed in carrying out the methods of the present invention may be prepared in accordance with techniques known to those skilled in the art,particularly in light of the disclosure and examples set forth below. Exemplary techniques for preparing the compounds are set forth in U.S. Pat. Nos. 5,602,172; 4,933,347; 5,723,495; 5,428, 051; 5,643,935; 5,639,755; 4,963,589; and 5,578,631, the disclosures of which are incorporated by reference herein in their entirety. For example, the compounds described in Formula (I) can be prepared by: (a) cyclodehydrative furanization of 1,4-diketones according to the procedure taught by R. E. Lutz, et al., *J. Am. Chem. Soc.* 56:2698 (1934) to form 2,5-bis-(4-bromophenyl)furan; (b) nitrilization of 2,5-bis(4-bromophenyl)furan using copper (I) cyanide to produce the corresponding bis-nitrile 2,5-bis-(4-cyanophenyl)furan; and (c) conversion of the bis-nitrile to the desired bis-dicationic aryl furan used in the invention.

According to a second method, compounds of Formula (I) may be prepared by (a) converting the appropriate bromoacetophenone to the ethyl bromophenyl-oxopropionate using sodium hydride and diethylcarbonate in tetrahydrofuran, (b) converting the ethyl bromophenyl-oxopropionate to the ethyl bis-bromobenzoyl-propionate using bromophenacyl bromide, (c) converting the bis-bromobenzoyl-propionate to the ethyl bis-bromophenyl furan using ethanol and hydrochloric acid, (d) hydrolysis of the ethyl bis-bromophenyl furan to the bis-bromophenyl furan carboxylic acid using potassium hydroxide followed by hydrochloric acid, (e) converting the carboxylic acid to the corresponding bis-nitrile with copper (I) cyanide and heat,and converting the bis-nitrile to the appropriate bis-dicationic aryl furan.

Conversion of the bis-nitrile to the bis-dicationic aryl furan of Formula (I) may be accomplished according to several methods known to those skilled in the art. According to one method, conversion of the bis-nitrile to the bis-dicationic aryl furan is carried out by conversion into intermediate imidate esters using classical Pinner methodology, followed by reaction of these intermediates with ammonia or the appropriate diamine for example, ethylenediamine, 1,3-propanediamine, etc. According to another method, the bis-nitrile is converted to the bis-dicationic aryl furan by fusion of the bis-nitrile directly with the hydrochloride salt of the appropriate diamine by thermolysis. This technique is particularly useful for the preparation of compounds wherein two R groups together form a cyclic alkyl.

Compounds described by Formulas (IV) and (V) can be prepared, for example, according to the following procedure with reference to Charts I–III described in U.S. Pat. No. 4,933,347. Such compounds can also be synthesized according to techniques described in U.S. Pat. No. 5,723,495. More specifically, the compounds may be prepared by first synthesizing known bis-nitriles using Allen's procedure for alkylation of phenols. See J. N. Ashley et al., *J. Chem. Soc.* 103–116 (1942); C. F. H. Allen et al., *Org. Synth. Coll. III,* (1955). The compounds can then be obtained by using variations of the known techniques of Clement and Raether and by using appropriate reagents. See B. Clement and W. Raether, *Arzneim. Forsch.* 35, 1009–1014 (1985).

EXAMPLES

The invention will now be described in greater detail with reference to the following examples. It should be noted that these examples are for illustrative purposes only, and are not meant to limit the invention.

Compounds used in the methods of the invention were synthesized in the laboratories of the inventors. The synthesis and physical properties for the following compounds have been previously described as follows: Compounds 1–4 & 7–14, 16–20 (Tidwell, R. R., *J. Med. Chem.,* 33: pp. 1252–1257 (1990)); Compound 15 (Jones, S. K., et al., *Antimicrob. Agents Chemother.* 34: pp. 1026–1030 (1990)); Compounds 21–27 (Berger, B. J., et al., *J. Pharmacol. Exp. Therapeut.* 256: pp. 883–889 (1991)); Compounds 28, 30, 32, and 47 (Fairley, T., et al., *J. Med. Chem.,* 36: pp.1746–1753 (1993); Tidwell, R. R., et al., *J. Med. Chem.* 21: pp.613–623 (1978)); Compounds 29, 31, 33, 34, and 48–50 (Fairley, T., et al., *J. Med. Chem.,* 36: pp.1746–1753 (1993)). The synthesis of the remaining compounds, 35–46, and 51–57, along with their physical properties are described below.

The compound melting points were recorded using a Thomas Hoover (Uni-Melt) capillary melting point apparatus and were not corrected. Proton ($^1$H) and Carbon ($^{13}$C) Nuclear Magnetic Resonance (NMR) spectra of the compounds were recorded employing a Varian GX400 spectrometer and chemical shifts (d) are given in ppm relative to tetramethylsilane (TMS). Coupling constants (J) are reported in Hertz. Mass spectra (MS) were recorded on a VG Instruments 70-SE spectometer (Georgia Institute of Technology, Atlanta, Ga.). IR spectra were recorded using a Michelson 100 (Bomen, Inc.) instrument. Elemental analysis was obtained from Atlantic Microlab In. (Norcross, Ga.) and are with in ±0.4 of the theoretical values. All chemicals and solvents were purchased from Aldrich Chemical Co., St. Louis, Mo. or Fisher Scientific, Pittsburgh, Pa.

Example 1

4-(N-cyclopentylamidino)-1,2-phenylene diamine hydrochloride

This compound is used as an intermediate in the synthesis of compounds 38, 42, 45, 54, and 56. Distilled cyclopentylamine (1.83 g, 0.021 mol) was added to a stirred suspension of the imidate ester hydrochloride (4.91 g, 0.02 mol) formed from 4-cyano-2-nitroaniline under Pinner type conditions in 30 ml of dry ethanol, the mixture was stirred for 12 h at room temperature and for 1 h at 50° C. The solvent was removed under reduced pressure and the residual thick oily mass was triturated with dry ether and dried under vacuum to yield 4.7 g (95%), mp 168–179° C. dec. $^1$H NMR (DMSO-d$_6$): 9.29 (br, 3H), 8.45(d, 2H, J=2.4), 803 (s, 2H), 7.77(dd.1H, J=2.4, 8.8), 4.20 (quintet,1H, J=6.0), 2.04–2.0 (m, 2H), 1.73–1.65 (m, 4H), 1.57–1.49 (m. 2H). $^{13}$C NMR (DMSO-d$_6$): 160.4, 148.5, 134.1, 129.4, 127.3, 118.9, 114.6, 54.1, 31.2, 23.5. The 4-(N-cyclopentylamidino)-2-nitroaniline (5.0 g, 0.02 mol) mp 238–240° C. dec; used directly without further characterization (5.0 g, 0.02 mol) and 1.0 g of 10% Pd/C in 130 ml of dry methanol was subjected to hydrogenation at 50 psi for approximately 1 h. The catalyst was filtered over Celite, washed with hot methanol and the solvent of the filtrate was removed under reduced pressure, the residue was triturated with dry ether, and the solid was filtered and dried under vacuum at 45° C. for 24 h. The yield of light brown hygroscopic solid was 3.91 g (72%); The compound yielded the following physical properties: mp 170–178° C. $^1$H NMR (DMSO-d$_6$): 8.97 (br s, 1H), 8.82 (br s, 1H), 8.64 (br s, 1H), 6.89 (s, 1H), 6.88 (d, 1H, J=8.4), 6.59 (d, 1H, J=8.4), 5.40 (br, 2H), 5.0 (br, 2H) 4.17 (m, 2H), 2.10–1.98 (m, 2H), 1.82–1.76 (m, 4H). $^{13}$C NMR (DMSO-d$_6$): 162.4, 140.8, 134.0, 118.4, 115.6, 113.0, 112.5, 53.7, 31.3, 23.5. MS(FAB) 219 (M$^+$+1). Anal. calc. for C$_{12}$H$_{18}$N$_4$.HCl.H$_2$O): C, 52.84; H, 7.76; N, 20.54. Found: C, 53.10; H, 7.77; N, 20.72.

Example 2

2,5-Bis[2-(5-amidino)benzimidazoyl]furan hydrochloride (Compound 35)

A solution of furan-2,5-dicaboxaldehyde (S. Morikawa, (1979) "Synthesis of hydroxymethylfural and 2,5- furandicarboxaldehydes", *Noguchi kenkyusho Jiho,* 21: pp. 25–33) (0.8 g 2 mmol), 4-amidino-1,2-phenylene diamino hydrochloride hydrate (0.8 g, 4 mmol) and 1,4-benzoquinone (0.432 g, 4 mmol) in ethanol (40 ml) was heated at reflux for 4 h (under nitrogen) (Bajic, M. et al., *Hetero. Com.* 1: 225–230 (1995)). The reaction mixture was cooled to room temperature and the dark solid was collected by filtration, washed with cold ethanol and then anhydrous ether, and dried to yield 0.55 g (71%) of the free base. This solid was dissolved slowly in hot ethanol (300 ml) and filtered. The filtrate volume was reduced to 70 ml and acidified with HCl saturated ethanol. After standing overnight in the refrigerator, the green solid was collected by filtration, washed with anhydrous ether and dried under vacuum to yield 0.4 g (52%) yield of solid. The compound demonstrated the following physical properties: mp>300° C. $^1$H NMR(DMSO-$d_6$): 9.30 (s, 4H); 8.19 (2s, 2H), 7.81, (d, 2H, J=8.8), 7.72 (d, 2H, J=8.4). 7.60 (s, 2H). $^{13}$C NMR (DMSO-$d_6$/$D_2$O): 166.8, 146.4, 146.1, 142.2, 139.7, 123.4, 122.7, 117.1, 116.1, 115.4, MS (FAB): m/z 385 (M$^+$+1); HRMS: calc. mass (free base) 385.1525 (M$^+$+1); observed mass: 385.1535. Anal. calc. for $C_{20}H_{16}N_8O$.2HCl.1.5$H_2O$: C, 49.59; H, 4.37; N, 23.14. Found: C, 49.40; H, 4.31; N, 22.96.

Example 3

2,5-Bis[2-{5-(2-imidazolino)}benzimidazoyl]furan hydrochloride (Compound 36)

A procedure similar to that described above was employed for the condensation of 2,5-furandicarboxaldehyde (S. Morikawa, (1979) "Synthesis of hydroxymethylfural and 2,5-furandicarboxaldehydes", *Noguchi kenkyusho Jiho,* 21: pp.25–33) and 2-(3,4-diaminophenyl)imidazoline (Fairley, T., (1993) *J. Med. Chem.,* 36: 1746–1753; Tidwell, R. R., (1978) *J. Med. Chem.,* 21:613–623) to give a 38% yield of a green powder. This compound demonstrated the following physical properties: mp<300° C., $^1$H NMR (DMSO-$d_6$): 10.53 (s,4H), 8.38 (s, 2H), 7.87 (d, 2H, J=8.5 ), 7.83(d, 2H, J=8.2 ), 7.62 (s, 2H), 4.04(s, 8H). $^{13}$MR (DMSO-$d_6$/$D_2$O): 166.3, 146.2, 146.1, 142.3,139.8,123.7, 117.6, 116.9, 116.1, 115.5, 45.0. MS (FAB): m/z 437 (M$^+$+1); HRMS: calc. mass (free base): 437.1838 (M$^+$+1); observed mass: 437.1832. Anal. calc. for $C_{24}H_{20}N_8O$.2HCl.5$H_2O$: C, 48.08; H, 5.38; N, 18.69. Found: C, 48.22; H, 5.25; N, 18.51.

Example 4

2,5-Bis[2-(5-N-isopropylamidino)benzimidazoyl] furan hydrochloride (Compound 37)

A procedure similar to that described above was employed for the condensation of 2,5-furandicarboxaldehyde (S. Morikawa, (1979) "Synthesis of hydroxymethylfural and 2,5-furandicarboxaldehydes", *Noguchi kenkyusho Jiho,* 21: pp.25–33) and 4-(N-isopropylamidino)-1,2-phenylene diamine (Fairley, T., (1993) *J. Med. Chem.,* 36: 1746–1753; Tidwell, R. R., (1978) *J. Med. Chem.,* 21:613–623) to give a 54% yield of a yellow-green powder. This compound displayed the following physical properties: mp>300° C. $^1$H NMR (DMSO-$d_6$): 9.60 (s, 1H), 9.58 (s, 1H), 9.45 (s, 2H), 9.04 (s, 2H), 8.06 (s, 2H), 7.82 (d, 2H, J=8.4), 7.69(s, 2H), 7.62 (d, 2H, J=8.2), 4.09 (m, 2H, J=7.0), 1.32 (d, 12H, J=6.3). $^{13}$C NMR (DMSO-$d_6$/$D_2$O): 162.8, 145.9, 145.1, 140.9, 138.5, 124.5, 124.0, 116.9, 115.9, 115.8, 45.9, 21.7. MS (FAB): m/z469 (M$^+$+1); HRMS: calc. mass (free base): 469.2464 (M$^+$+1); observed mass: 469.2475. Anal. calc. for: $C_{26}H_{28}N_8O$.3HCl.2.5$H_2O$: C, 50.12; H, 5.83; N, 17.99. Found: C, 50.45; H, 5.76 N, 17.64.

Example 5

2,5-Bis[2-(5-N-cyclopentylamidino)benzimidazoyl] furan hydrochloride (Compound 38)

A procedure similar to that described above in the previous examples was employed for the condensation of 2,5-furandicarboxaldehyde and 4-(N-cyclopentylamidino)-1,2-phenylene diamine to give a 77% yield of a yellow-green powder. The following physical properties were obtained: mp 287–289° C. dec. $^1$H NMR (DMSO-$d_6$/$D_2$O): 8.07 (s, 2H), 7.82 (d, 2H, J=8.4), 7.66 (s, 2H), 7.63 (d, 2H, J=8.4), 4.22–4.14 (m, 2H), 2.14–2.04 (m, 4H), 1.82–1.67 (m, 8H), 1.64–1.56 (m, 4H). $^{13}$C NMR (DMSO-$d_6$): 163.0, 145.4, 144.5, 140.4, 137.7, 123.9, 116.4, 115.5, 115.2, 54.6, 31.5, 23.7. MS (FAB) 521 (M$^+$+1). Anal. calc. for $C_{30}H_{32}N_8O$.4HCl: C, 54.06; H, 5.44; N, 16.81. Found: C, 53.80; H, 5.51; N, 16.68.

Example 6

2,5-Bis[2-(5-amidino)benzimidazoyl]pyrrole hydrochloride (Compound 39)

A procedure similar to that described in the above examples was employed for the condensation of 4-amidino-1,2-phenylene diamino hydrochloride hydrate (Fairley, T., (1993) *J. Med. Chem.,* 36: 1746–1753; Tidwell, R. R., (1978) *J. Med. Chem.,* 21:613–623) with pyrrole-2,-5-dicarboxaldehyde (Miller, R., (1981) *Acta Chem. Scand.,* B: 303–304) to yield 0.83 g (76%) of solid. The compound displayed the following physical properties: mp>300° C. $^1$H NMR (DMSO-$d_6$): 9.48 (br s, 1H), 9.18 (br s, 1H), 8.25 (s, 2H), 7.87 (d, J=8.4, 2H), 7.80 (dd, J=8.8 and 0.8, 2H).7.54 (s, 2H). MS (free base): m/e 384 (M$^+$+1). Anal., calc. for $C_{20}H_{17}N_9$.3HCl.3$H_2O$: C, 43.93; H, 4.73; N, 23.05. Found: C, 43.61; H, 4.62; N, 22.79.

Example 7

2,5-Bis[2-{5-(2-imidazolino)}benzimidazoyl]pyrrole hydrochloride (Compound 40)

A procedure similar to that described in the above examples was used for the condensation of pyrrole-2,5-dicarboxaldehyde and 2-(3,4-diaminophenyl)imidazoline (Fairley, T., (1993) *J. Med. Chem.,* 36: 1746–1753; Tidwell, R. R., (1978) *J. Med. Chem.,* 21:613–623) to give a 86% yield of solid. The compound dispalyed the following physical properties: mp>300° C. $^1$H NMR (DMSO-$d_6$): 10.71(s, 1H), 8.44 (s, 2H), 7.92 (dd, J=8.4 and 1.6, 2H), 7.86 (d, J=8.8, 2H), 7.39 (s, 2H), 4.04 (s, 8H). MS(free base): m/e 436 (M$^+$+1). Anal. calc. for $C_{24}H_{21}N_9$.3HCl.4$H_2O$: C, 46.72; H, 5.23; N, 20.43. Found: C, 46.49; H, 5.11; N, 20.28.

Example 8

2,5-Bis[2-(5-N-isopropylamidino)benzimidazoyl] pyrrole hydrochloride (Compound 41)

A procedure similar to that described in the above examples was used for the condensation of pyrrole-2,5-dicarboxaldehyde and 4-(N-isopropylamidino)-1,2-phenylene diamine (Fairley, T., (1993) *J. Med. Chem.,* 36:1746–1753; Tidwell, R. R., (1978) *J. Med. Chem.,* 21:613–623) to yield (79%) of a yellow-green solid. The compound displayed the following physical properties: mp 287–289° C. dec. $^1$H NMR (DMSO-$d_6$/$D_2$O): 8.06 (s, 2H), 7.81 (d, 2H, J=8.4), 7.65 (d, 2H, J=8.4), 7.41 (s, 2H), 4.06 (septet,2H, J=6.4), 1.30 (d, 12H, J=6.4). $^{13}$C NMR (DMSO-$d_6$/$D_2$O): 162.3, 145.8, 138.6, 135.7, 124.7, 124.2, 123.9, 115.7, 115.5, 114.9, 45.7, 21.4. MS (FAB) 468 (M$^+$+1). Anal. calc. for $C_{26}H_{29}N_9$.4HCl: C, 50.90; H, 5.42; N, 20.55. Found: C, 51.54; H, 5.57; N, 20.30.

Example 9

2,5-Bis[2-(5-N-cyclopentylamidino)benzimidazoyl] pyrrole hydrochloride (Compound 42)

A procedure similar to that described in the above examples was employed for the condensation of 4-(N-cyclopentylamidino)-1,2-phenylene diamine with pyrrole-2,-5-dicarboxaldehyde (Miller, R., (1981) *Acta Chem. Scand.,* B: 303–304) to yield (71%) a blue-green solid. The compound displayed the following physical properties: mp 290–294° C. $^1$H NMR (DMSO-$d_6$/$D_2$O): 8.0 (s, 2H), 7.77(d, 2H, J=8.4), 7.60 (d, 2H, J=8.4).7.32 (s, 2H), 4.09 (br m, 2H), 2.11–1.97 (m, 4H), 1.77–1.62 (m, 8H), 1.61–1.50 (m, 4H). $^{13}$C NMR (DMSO-$d_6$/$D_2$O): 163.1, 145.7, 138.6, 135.6, 124.6, 124.3, 123.8, 115.8, 115.5, 115.1, 55.0, 31.7, 23.9. MS (FAB) m/z 520 (M$^+$+1). Anal. calc. for $C_{30}H_{33}N_9$.4HCl.0.5$H_2$O: C, 53.42; H, 5.63; N, 18.68. Found: C, 53.90; H, 5.75; N, 18.16.

Example 10

1-Methyl-2,5-Bis[2-(5-amidino)benzimidazoyl] pyrrole hydrochloride (Compound 43)

A procedure similar to that described in the above examples was employed for the condensation of 4-amidino-1,2-phenylene diamine hydrochloride hydrate (Fairley, T., (1993) *J. Med. Chem.,* 36: 1746–1753; Tidwell, R. R., (1978) *J. Med. Chem.,* 21:613–623) with 1-methylpyrrole-2,-5-dicarboxaldehyde (Cresp, T. M., (1973) *J. Chem. Soc., Perkin Trans.* 1: 2961–2971) to give a 70% yield of product. The compound displayed the following physical properties: mp>300° C.; $^1$H NMR (DMSO-$d_6$): 9.38 (br s, 1H), 9.11 (br s, 1H), 8.19(s, 2H), 7.80 (d, J=8.4), 7.73 (dd, J=8 and 1.2, 2H), 7.33 (s, 2H), 4.72 (s, 3H). MS(free base): m/z 398 (M$^+$+1). Anal. calc. for $C_{21}H_{19}N_9$.3HCl.$H_2$O: C, 48.06; H, 4.61; N, 24.02. Found: C, 48.16; H, 4.58; N, 23.93.

Example 11

2,5-Bis[2-{5-(2-imidazolino)}benzimidazoyl]-1-methylpyrrole hydrochloride (Compound 44)

A procedure similar to that described in the above examples was employed for the condensation of 2-(3,4-diaminophenyl)imidazoline (Fairley, T., (1993) *J. Med. Chem.,* 36: 1746–1753; Tidwell, R. R., (1978) *J. Med. Chem.,* 21:613–623) with 1-methylpyrrole-2,-5-dicarboxaldehyde. A yield of 83% of solid mp >300° C. was obtained. The following additional physical properties were determined: $^1$H NMR(DMSO-$d_6$): 10.60 (s, 1H), 8.36 (s, 2H), 7.84 (dd, J=8.4 and 8, 4H), 7.30 (s, 2H), 4.72 (s, 3H), 4.04 (s, 8H). MS(free base): m/e 450 (M$^{+b\ +1}$). Anal. calc. for $C_{25}H_{23}N_9$.3HCl.3$H_2$O: C, 48.98; H, 5.26; N, 20.57. Found: C, 49.20; H, 4.79; N, 20.51.

Example 12

2,5-Bis[2-(5-N-cyclopentylamidino)benzimidazoyl] 1-methylpyrrole hydrochloride (Compound 45)

A procedure similar to that described in the above examples was employed for the condensation of 4-(N-cyclopentylamidino)-1,2-phenylene diamine with 1-methyl-2,-5-pyrrole dicarboxaldehyde (Cresp, T. M., (1973) *J. Chem. Soc., Perkin Trans.* 1: 2961–2971) to yield (85%) a blue solid having a mp of 324–326° C. The following additional physical properties were determined: dec. $^1$H NMR (DMSO-$d_6$/$D_2$O): 8.0 (s, 2H), 7.73 (d, 2H, J=8.4), 7.55 (d, 2H, J=8.4), 7.13 (s, 2H), 4.57 (s, 3H), 4.14 (quintet, 2H, J=5.2, 2.12–2.02 (m, 4H), 1.80–1.58 (m, 12H). MS (FAB) 534 (M$^+$+1). Anal. calc. for $C_{31}H_{35}N_9$.3HCl.$H_2$O, C: 56.32; H, 6.10; N, 19.07. Found: C 56.90; H 5.97; N 18.83.

Example 13

2,5-Bis[2-(5-N-isopropylamidino)benzimidazoyl] thiophene hydrochloride (Compound 46)

A procedure similar to that described in the above examples was employed for the condensation of 2,5-thiophenedicarboxaldehyde and 4-(N-isopropylamidino)-1, 2-phenylene diamine (Fairley, T., (1993) *J. Med. Chem.,* 36: 1746–1753; Tidwell, R. R., (1978) *J. Med. Chem.,* 21:613–623) to give a 75% yield of a green yellow solid mp 290–292° C. The physical properties for this compound were determined to be: dec. $^1$H NMR (DMSO-$d_6$/$D_2$O): 8.18 (s, 2H), 8.05 (s, 2H), 7.77 (d, 2H, J=8.4); 7.60 (d, 2H, J=8.4), 4.11 (quintet, 2H, J=6.4), 1.31 (d, 12H, J=6.4). MS (FAB) m/z 485 (M$^+$+1). Anal. calc. for $C_{26}H_{28}N_8S$.3HCl.$H_2$O. C, 51.02; H, 5.43; N, 18.31; Cl, 17.38. Found: C, 51.56; H, 5.54; N, 18.09; Cl, 17.37.

Example 14

2,6-Bis[2-{5-(2-imidazolino)}benzimidazoyl] pyridine hydrochloride (Compound 51)

A procedure similar to that described in the above examples was used for the condensation of 2,6-pyridine carboxyaldehyde and 2-(3,4-diaminophenyl)imidazoline (Fairley, T., (1993) *J. Med. Chem.,* 36: 1746–1753; Tidwell, R. R., (1978) *J. Med. Chem.,* 21:613–623) to give an 85% yield of solid mp>300° C. The physical properties for this compound were found to be: $^1$H NMR (DMSO-$d_6$): 10.71 (s, 1H), 8.51–8.49 (m, 4H), 8.30 (m, 1H), 7.96(m, 4H), 4.05(s, 8H). MS (free base): m/e 448(M$^+$+1). Anal. calc. for $C_{25}H_{21}N_9$.3HCl.3$H_2$O: C, 49.15; H, 4.94; N, 20.63. Found: C, 49.14; H, 4.68; N, 20.51.

Example 15

2,6-Bis[2-(5-amidino)benzimidazoyl]pyridine hydrochloride (Compound 52)

A procedure similar to that described in the above examples was used to condense 2,6-pyridine dicarboxaldehyde with 4-amidino-1,2-phenylene diamine hydrochloride hydrate (Fairley, T., (1993) *J. Med. Chem.,* 36: 1746–1753; Tidwell, R. R., (1978) *J. Med. Chem.,* 21:613–623) to yield 89% of a solid mp>300° C. The physical properties for this compound were determined to be: $^1$H NMR (DMSO-$d_6$): 9.45 (br s, 1H), 9.12 (br s, 1H), 8.51 (d, J=8, 2H), 8.34–8.28 (m, 3H), 7.94 (d, J=8.4, 2H), 7.79 (dd, J=8.4 and 1.6, 2H). MS(free base): m/z 396 (M$^+$+1). Anal. calc. for $C_{21}H_{17}N_9$.3HCl.3$H_2$O:C, 45.13; H, 4.69; N, 22.56. Found: C, 45.16; H, 4.58; N, 22.45.

Example 16

4,4'-Bis[2-(5-N-isopropylamidino)benzimidazoyl]-1, 2-diphenylethane hydrochloride (Compound 53)

1,2-Bis-(4-cyanophenyl)ethane was prepared in one step from 2,3-bis-(4-bromophenyl)propanoic acid (Dann, O., (1971) Liebigs Ann. Chem., 749: 68–89) by the action of CuCN in DMF (Das, B. P., et al., (1977) J. Med. Chem., 20: 531–536) in a 50% yield; mp 195–197° C. $^1$H NMR (DMSO-d$_6$): 7.68 (d, 4H, J=8), 7.40 (d, 4H, J=8), 3.01(s, 4H). $^{13}$NMR (DMSO-d$_6$): 146.7, 131.9, 129.3, 118.6, 108.6, 35.8. MS m/e 232 (M$^+$+1).1,2-Bis-(4-cyanophenyl)ethane was used without further characterization and on treatment with DIBAL gave a white crystalline solid (CHCl$_3$:ether) 76% mp 121–122° C. of 1,2-bis-(4-formylphenyl)ethane. $^1$H NMR (DMSO-d$_6$): 9.96 (s, 2H), 7.80 (d, 4H, J=8), 7.44 (d, 4H J=8), 3.05 (s, 4H). $^{13}$C NMR (DMSO-d$_6$/D$_2$O): 192.0, 184.0, 134.2, 129.1, 128.8, 36.0. Anal. Calc. for C$_{16}$H$_{14}$O$_2$.0.1H$_2$O: C, 80.04; H, 5.96. Found: C, 80.09; H, 5.98. A protocol similar to that described above was employed for the condensation of 1,2-bis-(4-formylphenyl) ethane and 4-(N-isopropylamidino)-1,2-phenylene diamine (18, 35). A 75% yield of a purple solid mp>320° C. $^1$H NMR (DMSO-d$_6$/D$_2$O): 8.09 (d, 4H, J=8), 8.06 (s, 2H), 7.83 (d, 2H, J=8.4), 7.65 (d, 2H, J=8.4), 7.48 (d, 4H, J=8), 4.03 (br m, 2H), 3.07 (br, 4H), 1.29 (d, 12H, J=6). $^{13}$NMR (DMSO-d$_6$/D$_2$O): 162.4, 153.0, 146.6, 138.3, 135.4, 129.8, 127.9, 124.8, 124.1, 123.5, 115.5, 115.0, 45.6, 36.2, 21.2. MS (FAB) 583 (M$^+$+1)Anal. calc. for C$_{36}$H$_{38}$N$_8$.4HCl.0.5H$_2$O: C, 58.61; H, 5.87; N, 15.19. Found: C, 58.31; H, 5.79; N, 15.02.

Example 17

4,4'-Bis[2-(5-N-cyclopentylamidino)benzimidazoyl]-2,5-diphenylfuran hydrochloride (Compound 54)

2,5-Bis(4-formylphenyl)furan was prepared by reduction of 2,5-bis-(4-cyanophenyl)furan (Bajic, M., (1996) Heterocyclic Com. 2: 135–140) (1.12 g 0.004 mol) using 1M DIBAL in CH$_2$Cl$_2$ (1.83 g, 0.012 mol) to yield a pale yellow solid, 0.77 g (70%), mp 173–4° C. (CHCl$_3$:ether). $^1$H NMR (DMSO-d$_6$/D$_2$O) 10.0 (s, 2H), 8.05 (d, 4H, J=7.5), 7.97 (d, 4H, J=7.5), 7.37 (s, 2H). $^{13}$C NMR (DMSO-d$_6$/D$_2$O) 192.0, 125.7, 135.0, 134.6, 130.1, 123.9, 111.6. MS m/e 276. Anal. calc. for C$_{18}$H$_{12}$O$_3$:C, 91.49; H, 5.12. Found: C, 91.22; H, 5.38.

A procedure similar to that described in the above examples was employed for the condensation of 4-(N-cyclopentylamidino)-1,2-phenylene diamine with 2,5-bis(4-formylphenyl)furan to yield (77%) of a yellow solid mp 295–297° C. dec. $^1$H NMR (DMSO-d$_6$/D$_2$O): 8.30 (d, 4H, J=8.4), 8.05 (d, 4H, J=8.4), 8.01 (s, 1H), 7.77 (d, 2H, J=8.4), 7.56 (d, 2H, J=8.4), 7.27 (s, 2H), 4.15 (br, 2H), 2.13–2.03 (m, 4H), 1.81–1.55 (m, 12H). $^{13}$C NMR (DMSO-d$_6$/D$_2$O): 163.7, 154.0, 153.1, 141.2, 138.6, 132.8, 127.9, 126.1, 124.6, 123.3, 123.1, 115.9, 115.7, 111.0, 55.7, 32.3, 24.4. MS (FAB) m/z 673 (M$^+$+1). Anal. calc. for C$_{42}$H$_{40}$N$_8$.4HCl: C, 61.61; H, 5.42; N, 13.69. Found: C, 62.28; H, 5.74; N, 13.62.

Example 18

2,5-Bis[2-(5-amidino)benzimidazoyl]benzo[b]furan hydrochloride (Compound 55)

A procedure similar to that in the above-described examples was employed for the condensation of benzo[b]furan-2,5-dicarboxaldehyde and 4-amidino-1,2-phenylene diamine hydrochloride hydrate to give a 70% yield of a blue-gray solid mp 338–340° C. dec. $^1$H NMR (DMSO-d$_6$/D$_2$O) 8.6 (s, 1H), 8.27(d,1 H, J=8), 8.19 (d, 2H, J=9.6), 7.89 (d,1 H, J=8.8), 7.87 (s, 1H), 7.87(d, 1H, J=8.4), 7.78 (d, 1H, J=8.4).7.73 (d, 1H, J=8.8), 7.68 (d, 1H, J=8). $^{13}$C NMR (DMSO-d$_6$/D$_2$O) 166.4, 165.9, 156.6, 153.5, 147.4, 145.4, 141.6, 139.9, 139.1, 136.9, 128.6, 126.2, 123.3, 122.9, 122.6, 122.2, 122.1, 116.9, 115.8, 115.5, 115.0, 112.8, 108.6. MS(FAB) 435 (M$^+$+1). Anal. calc. for C$_{24}$H$_{18}$N$_8$O.3HCl.H$_2$O: C, 51.30; H, 4.12; N, 19.94. Found: C,51.72; H, 4.14; N, 15.64.

Example 19

2,5-Bis[2-(5-N-cyclopentylamidino)benzimidazoyl]benzo[b]furan hydrochloride (Compound 56)

2-Acetyl-5-bromobenzo[b]furan was prepared as reported in the literature (Dann, O., (1972) Liebigs Ann. Chem., 760:37–87) in an 86% yield; mp 110–111° C. (lit=108–111° C.) $^1$H NMR (DMSO-d$_6$): 8.02 (d, 1H, J=1.6), 7.79 (s, 1H), 7.68(d,1 H, J=9.2), 7.65 (dd,1H, J=9.2, 1.6), 2.58 ( s, 3H). $^{13}$C NMR (DMSO-d$_6$): 181.6, 153.5, 152.9, 130.9, 128.8, 125.7, 115.9, 114.1, 112.9, 26.2. MS m/z 239(M$^+$). The acetyl compound was converted into 5-bromobenzo[b]furan-2-carboxylic acid in a 77% yield as reported (15) mp 258–262° C. (lit=258–262° C.). $^1$H NMR (DMSO-d$_6$/D$_2$O): 7.95 (d, 1H, J=1.6), 7.64 (d, 1H, J=8.8), 7.58 (dd, 1H, J=8.8, 1.6), 7.57 (s, 1H). $^{13}$C NMR (DMSO-d$_6$/D$_2$O): 159.5, 153.6, 147.3, 129.9, 128.9, 125.2, 115.8, 113.9, 112.5. MS m/z 241(M$^+$).5-Bromobenzo[b]furan-2-carboxylic acid, used without further characterization, was converted, using standard procedures via the acid chloride, into 5-bromo-2-carboxamidobenzo[b]furan in a 81% yield; mp 208–210° C. $^1$H NMR (DMSO-d$_6$): 8.2 (br s, 1H), 7.99 (s, 1H), 7.77 (br s, 1H), 7.61 (d, 1H, J=8.8), 7.57(dd, 1H, J=8.8, 2) 7.51 (s,1H). $^{13}$C NMR (DMSO-d$_6$/D$_2$O): 159.4, 153.0, 150.5, 129.4, 128.3, 125.2, 115.9, 113.9, 109.0. MS m/e 240 (M$^+$). The amide, used without further characterization, was dehydrated employing POCl$_3$ to form 5-bromo-2-cyanobenzo[b]furan in a 88% yield; mp 147–148° C. $^1$H NMR (DMSO-d$_6$) 8.0 (s, 1H), 7.97 (s, 1H), 7.67 (br s, 2H). $^{13}$C NMR (DMSO-d$_6$) 153.7, 131.1 127.2, 127.1, 125.2, 118.8, 116.7, 113.7, 111.1. MS m/e 222(M$^+$). 5-Bromo-2-cyanobenzo[b]furan, used without further characterization, was converted via a standard procedure (Newman, M. S., (1961) J. Org. Chem., 26:2525) into 2,5-dicyanobenzo[b]furan in a 79% yield; mp 166–167° C. $^1$H NMR (DMSO-d$_6$): 8.39 (s, 1H), 8.14 (s, 1H), 7.97 (d, 1H, J=8.8) 7.92 (d, 1H, J=8.8). $^{13}$C NMR (DMSO-d$_6$): 156.3, 131.5 128.5, 128.2, 125.8, 119.3, 117.9, 113.4, 110.8, 107.7. MS m/e 168 (M$^+$). Anal. calc. for C$_{10}$H$_4$N$_2$O: C, 71.42; H, 2.39; N, 16.16. Found: C, 71.78; H, 2.46; N, 16.51. 2,5-Diformylbenzo[b]furan was prepared by reduction of the bis-nitrile using DIBAL which was added dropwise to a stirred solution of the bis-nitrile (1.68 g, 0.01 mol) in 150 ml dry methylene chloride under nitrogen. The mixture was stirred for 15 min, allowed to reflux for 40 min and the mixture was cooled. 100 ml of 1M H$_2$SO$_4$ was added dropwise while maintaining the solution temperature below 25° C. The methylene chloride layer was separated, the aqueous layer was extracted with 100 ml of methylene chloride, and the combined organic phases were washed with 20% NaHCO$_3$, and dried over Na$_2$SO$_4$. The solvent was removed under reduced pressure and the residue was triturated with 1:1 ether:hexane. The resulting white solid was filtered, dried in a vacuum to yield 1.2 g ( 69%) mp 141–142° C. $^1$H NMR (DMSO-d$_6$): 10.1 (s, 1H), 9.92 (s, 1H), 8.48 (d, 1H, J=0.8), 8.10 (s, 1H), 8.08 (dd, 1H, J=0.8, 8.88), 7.90 (d, 1H, J=8.8). $^{13}$C NMR (DMSO-d$_6$): 191.8, 180.6, 158.1, 153.6, 132.9, 128.9, 127.5, 126.9, 118.8, 113.1. Anal. calc. for C$_{10}$H$_6$N$_2$.0.2H$_2$O: C, 67.75; H, 3.67. Found: C, 67.83; H, 3.59. A protocol similar to that described above was employed for the condensation of 4-(N-cyclopentylamidino)-1,2-phenylene diamine with benzo[b]furan-2,5-dicarboxaldehyde to yield a gray solid in a 73% yield; mp 290–292° C. dec. $^1$H NMR (DMSO-d$_6$/D$_2$O): 8.62 (s, 1H), 8.27(d, 1H, J=8.8), 8.08 (s, 1H), 8.05 (s, 1H), 7.95 (d, 1H, J=8.8), 7.90 (s, 1H), 7.84 (d, 1H, J=8.8), 7.79 (d, 1H, J=8.4), 7.64 (d, 1H, J=8.4 ).7.57 (d, 1H, J=8.8), 4.14 (br 2H), 2.13–2.06 (m, 4H), 1.81–1.56 (m, 12H). $^{13}$C NMR (DMSO-d$_6$/D$_2$O): 163.4, 163.1, 156.9, 153.2, 147.6, 145.2, 141.2, 138.8, 136.2, 128.9, 126.5, 124.5, 124.1 123.9, 123.5 122.5, 122.4, 116.9, 116.1, 115.8, 115.7, 115.1, 113.2, 108.8, 54.9, 54.8, 31.7, 23.9. MS(FAB) m/z 571 (M$^+$+1). Anal. calc. for C$_{34}$H$_{34}$N$_8$O.4HCl: C, 56.99; H, 5.34; N, 15.64. Found: C, 56.89; H, 5.34; N, 15.53.

Example 20

2,7-Bis[2-(5-N-isopropylamidino)benzimidazoyl] fluorene hydrochloride (Compound 57)

A mixture of 2,7-dibromofluorene 6.48 g (0.02 mol) and cuprous cyanide 5.37 g (0.06 mol) in 35 ml quinoline was heated under reflux for 2 h (followed by Thin Layer Chromatography, silica gel Kodak), benzene mobile phase). The mixture was cooled and extracted with 2×150 ml chloroform. The organic layer was stirred with 200 ml 2M.HCl for 2 h, washed with water, dried over anhydrous Na$_2$SO$_4$, filtered, dried, concentrated, redissolved in minimum amount of chloroform, and chromatographed over neutral alumina. The column was first eluted with hexane:ether (2:1) to remove residual quinoline and finally with ether: CHCl$_3$(1:1) to CHCl$_3$ to afford fluffy pale solid 2.72 g (63%) mp 282–4° C. of 2,7-dicyanofluorene. $^1$H NMR (DMSO-d$_6$/D$_2$O): 8.16 (d, 2H, J=8.4), 8.04 (s, 2H), 7.83 (d, 2H, J=8.4), 4.07 (s, 2H). $^{13}$C NMR (DMSO-d$_6$/D$_2$O): 144.2, 143.3, 130.8, 128.5, 121.7, 118.5, 110.1, 36.0. MS m/z 216 (M$^+$). Anal. calc. for C$_{15}$H$_8$N$_2$: C, 83.21; H, 3.72; N, 12.95. Found: C, 83.21; H, 3.78; N, 12.99. To a stirred solution of 2,7-dicyanofluorene (2.16 g, 0.01 mol) in 150 ml of dry CH$_2$Cl$_2$ was added DIBAL (1M in cyclohexane, 4.26 g, 0.03 mol) under nitrogen at room temperature. The suspension was heated at 40° C. for 1 h, cooled, 100 ml 1M H$_2$SO$_4$was added dropwise and stirred for 1 h, the precipitated yellow solid was filtered, recrystallized from CHCl$_3$:ether to yield 2,7- diformylfluorene as pale crystalline solid, mp 218–220° C., 1.6 g (72%). $^1$H NMR (DMSO-d$_6$/D$_2$O) 10.08 (s, 2H), 8.16 (d, 2H, J=8.0), 8.11 (s, 2H), 7.95 (d, 2H, J=8.0), 4.10 (s, 2H). $^{13}$C NMR (DMSO-d$_6$/D$_2$O) 191.9, 145.0, 144.7, 135.6, 128.5, 125.4, 121.1, 36.0. MS m/e 222 (M$^+$). Anal. calc. for C$_{15}$H$_{10}$O$_2$0.1H$_2$O: C, 80.41; H, 4.49. Found: C, 80.32; H, 4.63. A procedure similar to that in the above-described examples was used for the condensation of 2,7-diformylfluorene and 4-(N-isopropylamidino)- 1,2-phenylene diamine to yield (72%) of a green solid mp 310–313° C. dec. $^1$H NMR (DMSO-d$_6$/D$_2$O): 8.53 (s, 2H), 8.34 (d, 2H, J=8.4), 8.22 (d, 2H, J=8.4), 8.11 (s, 2H), 7.85 (d, 2H, J=8.4), 7.65 (d, 2H, J=8.4), 4.23 (s, 2H), 4.09 (quintet,2H, J=6.4), 1.33 (d, 12H, J=6.4). $^{13}$C NMR (DMSO-d$_6$/D$_2$O) 162.2, 153.1, 144.9, 143.5, 138.7, 136.3, 126.9, 125.7, 124.3, 123.6, 121.7, 115.6, 114.7, 45.3, 36.7, 21.1. MS m/z (FAB) 567 (M$^+$+1). Anal. calc. for C$_{35}$H$_{34}$N$_2$.4HCl: C, 58.99; H, 5.37; N, 15.73. Found: C, 59.14; H, 5.59; N, 15.43.

Examples 21–25

Compounds described in these examples were synthesized in the laboratories of the inventors. Stock solutions of 10,000 μg were made in sterile distilled water or dimethyl sulfoxide (DMSO). The solutions were filter sterilized by passage through a 0.22 μm Millex Durapore membrane filter, and stored at −70° C. until use. The synthesis and physical properties for the following compounds are set forth in the following references: compounds 1–15 (Patrick, D. A., et al., *Eur. J. Med. Chem.*, 32: pp.781–793 (1997)); compounds 16 and 17 (Das, B. P., et al., *J. Med. Chem.*20: pp.531–536 (1977)); compound 18 (Boykin, D. W., et al., *Biorg. and Med. Chem. Letters* 6: pp.3017–3020 (1996)); compounds 19 and 25 (Trent,J. O., et al., *J. Med. Chem.*39: pp.4554–4562 (1996)); compounds 20–24 (Boykin, D. W., et al., *J. Med. Chem.*, 41: pp.124–129 (1998)); compounds 48–63 (Czarny, A. W., et al., *J. Heterocyclic Chemistry*, 33: pp.1393–1397 (1996)), and compounds 64–67 (Tidwell, R. R., et al., *J. Med. Chem.*, 21: pp.613–623 (1978). A brief description of the synthesis and physical properties of the other compounds (33–38, and 40–41) is as follows.

Melting points were recorded using a Thomas Hoover (Uni-Melt) capillary melting point apparatus or a Fischer-Johns apparatus and are uncorrected. $^1$H NMR and 13C NMR spectra were recorded employing a Varian GX400 spectrometer and chemical shifts (δ) are in ppm relative to TMS and coupling constants (J) are reported in Hertz. Mass spectra were recorded on a VG Instrument 70-SE spectrometer (Georgia Institute of Technology, Atlanta, Ga.). IR spectra were recorded using a Michelson 100 instrument (Bomem, Inc.). Elemental analysis were obtained from Atlanta Microlab Inc. (Norcross, Ga.) and are within a tolerance of 0.4 of the theoretical values. All chemicals and solvents were Aldrich Chemical Co. or Fisher Scientific.

In Examples 21–25, to a suspension of 2,5-bis[4-carboxyphenyl]furan diacid chloride (0.69 g, 0.002 mol) in 75 ml dry CH$_2$Cl$_2$ a substituted diamine (0.002 mol) was added, the mixture was stirred at room temperature for 6 h. The solvent was removed by distillation, the residue was treated with ice-water, the pH of the mixture was adjusted to 10 with 2M NaOH and the separated solid was filtered, washed with cold water and crystallized from ether: CHCl$_3$ or ether:methanol to yield pale yellow solids in yields of 75–85%. The free base was converted to its HCl salt by treating with saturated ethanolic-HCl in yields of 75–90% .

Example 21

2,5-Bis-[4-(3-(N-morpholinopropyl)carbamoyl) phenyl]furan dihydrochloride (Compound 33)

An 83% yield of yellow crystalline solid mp 140–142° C. dec was obtained using a procedure described above. The following data was obtained: $^1$H NMR (DMSO-d$_6$/D$_2$O) 7.93 (d, 4H, J=8.4), 7.86 (d, 4H, J=8.4), 7.15 (s, 2H), 3.86 (br m, 8H), 3.38 (br m, 12H), 3.16 (t,4H, J=7.6), 2.0 (quintet, 4H, J=7.6). $^{13}$C NMR (DMSO-d$_6$/D$_2$O) 166.5, 152.7, 133.1, 132.4, 128.0, 123.4, 110.0, 63.3, 54.3, 51.3, 36.6, 23.4. MS m/e 560 (M$^+$). Anal. calcd. for C$_{32}$H$_{40}$N$_4$O$_5$!2HCl C, 60.65; H, 6.68; N, 8.84. Found: C, 60.59; H, 6.77; N, 8.87.

Example 22

2,5-Bis[4-(2-N, N-dimethylaminoethylcarbamoyl) phenyl]furan dihydrochloride (Compound 34)

The procedure used for Example 21 was followed and an 80% yield of pale yellow crystalline solid mp 189–191° C. dec was obtained. The following data was obtained: $^1$H NMR (DMSO-d$_6$/D$_2$O) 7.94 (d, 4H, J 8.4), 7.84 (d, 4H, J=8.4), 7.12 (s, 2H), 3.66 (t,4H, J=6.0), 3.30 (t,4H, J=6.0), 2.84 (s, 12H). $^{13}$C NMR (DMSO-d$_6$/D$_2$O) 167.4, 152.9, 132.9, 132.7, 128.4, 123.7, 110.4, 56.6, 43.1, 34.9. MS m/e 448 (M$^+$). Anal. calcd. for $C_{26}H_{32}N_4O_3$!2HCl C, 59.88; H, 6.57; N, 10.74. Found: C, 59.78; H, 6.66; N, 10.64.

Example 23

2,5-Bis[4-(3-N,N-dimethylaminopropylcarbamoyl)phenyl]furan dihydrochloride (Compound 35)

The procedure used in Example 21 was followed and a 75% yield of yellow hygroscopic solid mp 205–208° C. dec was obtained. The following data were also obtained: $^1$H NMR (DMSO-d$_6$) 10.91 (br, 2H), 8.80 (b s 2H), 8.03 (d, 4H, J=8.4), 7.92 (d, 4H, J=8.4), 7.23 (s, 2H), 3.40 (q, 4H, J=6), 3.15 (quintet,4H, J=5.2), 2.76 (s, 6H), 2.75 (s, 6H), 2.02 (quintet,4H, J=6.8). $^{13}$C NMR (DMSO-d$_6$/D$_2$O) 165.6, 152.4, 132.8, 131.9, 127.7, 122.9, 109.6, 54.3, 41.7, 36.2, 23.8. MS m/e 476 (M$^+$). Anal. calcd. for $C_{28}H_{36}N_4O_3$!2HCl!0.5H$_2$O C, 60.21; H, 7.03; N, 10.03. Found: C, 60.51; H 7.13; N, 9.95.

Example 24

2,5-Bis[4-(3-N-methyl-3-N-phenylaminopropylcarbamoyl)phenyl]furan dihydrochloride (Compound 36)

The procedure used for Example 21 was employed and a 78% yield of yellow solid, 85–88° C. dec was obtained. The following data was also obtained: $^1$H NMR (DMSO-d$_6$/D$_2$O) 7.93 (d, 4H, J=8.4), 7.89 (d, 4H, J=8.4), 7.58 (d, 2H, J=8.8), 7.55-7.48 (m, 6H), 7.37 (S, 2H), 7.18 (s, 2H), 3.59 (m, 4H), 3.35 (t,4H, J=7.2), 3.16 (s, 6H), 1.83 (quintet,4H, J=7.2). $^{13}$C NMR (DMSO-d$_6$/D$_2$O) 166.4, 152.7, 133.1, 132.4, 130.1, 130.0, 128.0, 123.4, 119.7, 109.9, 55.3, 43.6, 36.5, 25.3. MS m/e. Anal. calcd for: $C_{38}H_{40}N_4O_3$!2HCl!0.75H$_2$O C; 66.37; H, 6.34; N, 8.15. Found: C, 66.43; H, 6.34; N, 8.21.

Example 25

2,5-Bis[4-(3-N, N$^8$,N$^{11}$-trimethylaminopropylcarbamoyl)phenyl]furan dihydrochloride (Compound 37)

The procedure used in Example 21 was employed and an 85% yield of yellow solid mp 245–247° C. dec was obtained. The following data were also obtained: $^1$H NMR (DMSO-d$_6$/D$_2$O) 7.82 (d, 4H, J=8), 7.56 (d,4H, J=8), 7.07 (s, 2H), 3.5–3.48 (m, 4H), 3.03 (brm, 4H), 2.94 (s, 6H ), 2.76 (s, 12H), 1.98 (quintet,4H, J=7.6). $^{13}$C NMR (DMSO-d$_6$/D$_2$O) 171.2, 152.8, 135.4, 131.2, 127.9, 123.8, 109.7, 54.9, 42.7, 38.7, 22.4. MS m/e 504 (M$^+$). Anal. Calcd. For: $C_{30}H_{40}N_4O_3$!2HCl!0.5H$_2$O. C, 61.42; H, 7.38; N, 9.45. Found: C, 61.11; H, 7.27; N, 9.61.

Example 26

2,5-Bis[3-amidinophenyl]furan dihydrochloride (Compound 38)

A suspension of the imidate ester dihydrochloride(0.87 g, 0.002 mol), prepared from 2,5-bis[3-cyanophenyl]furan in 30 ml absolute ethanol was saturated with dry ammonia at 0–5° C. and the mixture was stirred at room temperature for 2 h. The solvent was removed and the solid was treated with ice-water, filtered, basified with cold aqueous 2 M NaOH and the off-white precipitate which formed was filtered. The solid was washed with water and dried to yield 0.49 g (80.6%), mp 198–200 C. The free base (0.3 g, 0.001 mol) was converted into the HCl salt by treating with ethanolic HCl to yield 0.35 g (90%) mp 221–2240° C. dec. the following data was obtained: $^1$H NMR (DMSO-d$_6$/D$_2$O) 8.18 (br s, 2H), 8.10 (d, 2H, J=7.6), 7.68 (t, 2H, J=7.6), 7.64 (d, 2H, J=7.6), 7.14 (s, 2H) . $^{13}$C NMR (DMSO-d$_6$) 166.1, 152.5, 131.3, 130.6, 129.3, 129.0, 127.4, 123.3, 110.5. MS (FAB) m/e 305 (M$^+$+1). Anal. Calcd. For: $C_{18}H_{16}N_4O$!2HCl!0.25H$_2$O. C, 56.55; H, 4.88; N, 14.67. Found: C, 56.75; H, 4.84; N, 14.26.

Example 27

2,5-Bis-[3-(N-isopropylamidino)amidinophenyl]furan dihydrochloride (Compound 40)

The imidate ester hydrochloride (0.435 g, 0.001 mol), prepared from 2,5-bis[3-cyanophenyl]furan and isopropyl amine (0.124 g, 0.0022 mol) in 10 ml ethanol were stirred for 12 h and yielded, after standard work-up, 0.13 g (80%) of beige free base having a mp 180–181 C. (crystallized from hexane:ether 3:1). The free base on treatment with saturated ethanolic HCl yielded 0.29 g (75%) crystalline solid, mp 225–227 C. dec. The following additional data were also obtained: $^1$H NMR (DMSO-d$_6$) 8.18–8.12 (m, 4H), 7.71–7.62 (m, 4H), 7.27 (s, 2H), 4.09 (quintet,2H, J=6.4), 1.30 (d, 12H, J=6.4). $^{13}$C NMR (DMSO-d$_6$) 161.6, 152.1, 130.4, 129.9, 129.7, 127.9, 127.3, 123.3, 110.1, 45.2, 21.2.MS (FAB) m/e 339 (M$^+$+1). Anal. calcd. for: $C_{24}H_{28}N_4O$!2HCl!0.25H$_2$O (465.92) C, 61.86; H, 6.59; N, 12.02. Found: C, 61.82; H, 6.27; N, 11.76.

Example 28

2,5-Bis[3[(N-(2-dimethylaminoethyl)amidino]phenylfuran dihydrochloride (Compound 41)

A mixture of imidate ester hydrochloride (0.435 g, 0.001 mol), prepared from 2,5-bis[3-cyanophenyl]furan and 2-dimethylaminoethylamine (0.185 g, 0.0021 mol) in 10 ml ethanol was stirred at room temperature for 12 h. Subsequent to standard work up, 0.33 g (74%) crystalline solid mp 75–77° C. was obtained. The free base (0.30 g, 0.00072 mol) on treatment with saturated ethanolic HCl yielded 0.35 g (82%) of hydrochloride salt (very hygroscopic) which was dried at 75° C. for 24 h; mp 260–263° C. dec. The following additional data were also obtained: $^1$H NMR (DMSO-d$_6$) 8.28(brs,2H), 8.12 (d, 2H, J=8), 7.72 (d, 2H, J=8), 7.65 (t,2H, J=8), 7.21 (s, 2H), 3.9 (t,4H, J=4.2), 3.50 (t,3H, J=4.2), 2.89 (s, 12H). $^{13}$C NMR (DMSO-d$_6$) 164.1, 152.4, 130.9, 130.3, 129.6, 128.8, 127.6, 123.7, 110.5, 54.5, 43.2, 38.4. MS (FAB) m/e 447 (M$^+$+1). Anal. calcd. for: $C_{26}H_{34}N_6O$!4HCl (592.44) C, 52.70; H, 6.46; N, 14.19. Found: C, 52.43; H, 6.42; N, 13.99.

Examples 1–20

Antifungal Test Results

Antifungal susceptibility testing for compounds set forth in Examples 1–20 is discussed hereinbelow. The fungi that were employed included two reference strains, *C. neoformans* var. *neoformans* H99 and *C. albicans* A39 and the following clinical isolates: (1) two strains of fluconazole-resistant *C. neoformans* var. *neoformans* (135.95 and 114.96); (2) two strains of *C. neoformans* var. *gattii* (119.95 and 114.95); (3) two strains of fluconazole-resistant *C. albicans* (102.96 and 103.96); and (4) one strain each of *Torulopsis glabrata* (142.91), *Candida parapsilosis* (111.96), *Candida krusei* (132.91), *C. tropicalis* (110.96), *Candida lusitaniae* (111.92), *Fusarium solani* (152.89), Aspergillus fumigatus (168.95), and Aspergillus flavus (112.96). Antifungal susceptibility testing was performed using an RPMI-1640 medium (Sigma Chemical Co., St. Louis, Mo.) with glutamine, without sodium bicarbonate, and buffered at pH 7.0 with 0.165 M morpholine-propanesulfonic acid (MOPS).

In vitro susceptibility testing in the form of Minimum Inhibitory Concentration (MIC) experiments were performed using the broth macrodilution method according to the recommendations of the National Committee for Clinical Laboratory Standards (see 1995 manual). The only difference compared to the standardized procedure was the choice of drug dilutions ranging from 100 to 0.09 µg/ml. Briefly, this procedure specifies an inoculum grown at 35° C. and adjusted to a concentration of $0.5-2.5\times10^3$ CFU/ml with an incubation of the test performed at 35° C. and reading at 48 hours for all yeasts except for C. neoformans which is interpreted at 72 hr. The MIC was defined as the lowest drug concentration which showed a visual turbidity less than or equal to an 80 percent inhibition compared to that produced by the growth control tube.

Minimum Fungicidal Concentration (MFC) experiments were adapted from a method by McGinnis (McGinnis, M. R., (1980) "Susceptibility testing and bioassay procedure", p. 431, Academic Press, Inc., New York). Briefly, 10 µl aliquots from tubes with growth inhibition were plated onto Sabouraud agar plates. The lowest drug concentration that yielded three or fewer yeasts colonies was recorded as the MFC.

Molds were tested by the National Committee for Clinical Laboratory Standards method cited above using the below-referenced modifications. Isolates were grown on Sabouraud dextrose agar at 30° C. and subcultured twice to insure viability. After adequate sporulation occurred (4–12 days), conidia were harvested by flooding colonies with a sterile solution of 0.85 percent NaCl and 0.05 percent Tween 80 in sterile distilled water. Inocula were prepared using a hemocytometer for counting, then diluted with RPMI 1640 medium to obtain a final inoculum size of approximately $0.5-2.5\times10^3$ CFU/ml. The inoculum size was verified by plating an aliquot of the inoculum. Tests were incubated at 30° C. for 48–72 h or until growth in the control tube was visible. In each experiment, the quality control included the testing of C. albicans A 39 and C. neoformans H99 against fluconazole and amphotericin B.

Examples 21–28

Antifungal Test Results

Antifungal susceptibility testing for compounds set forth in Examples 21–28 is discussed hereinbelow. The fungi that were employed included two quality control reference strains, C. neoformans var. neoformansH99 and C. albicans A39 and the following clinical isolates: (1) four strains of C. neoformans var. neoformans (167.95; 135.95; 114.96; and 133.95) of which three were fluconazole-resistant>64 µg/ml (135.95; 114.96; and 133.95); (2) two strains of C. neoformans var. gattii (119.95 and 114.95); (3) two strains of fluconazole-resistant>64 µg/ml C. albicans (102.96 and 103.96); and (4) one strain each of C. glabrata (142.91), Candida parapsilosis (111.96), Candida krusei (132.91), C. tropicalis (110.96), Candida lusitaniae (111.92), Fusarium solani (152.89), Aspergillus fumigatus (168.95), Rhizopus arrhizus (117.89), Paecilomyces lilacinus (137.90), and Aspergillus flavus (112.96). Antifungal susceptibility testing was performed using an RPMI-1640 medium (Sigma Chemical Co., St. Louis, Mo.) with glutamine, without sodium bicarbonate, and buffered at pH 7.0 with 0.165 M morpholinepropanesulfonic acid (MOPS).

In vitro susceptibility testing in the form of Minimum Inhibitory Concentration (MIC) experiments were performed using the broth macrodilution method according to the recommendations of the National Committee for Clinical Laboratory Standards (see 1995 manual). The only difference compared to the standardized procedure was the choice of drug dilutions ranging from 100 to 0.09 µg/ml. Briefly, this procedure specifies an inoculum grown at 35° C. and adjusted to a concentration of $0.5-2.5\times10^3$ CFU/ml with an incubation of the test performed at 35° C. and reading at 48 hours for all yeasts except for C. neoformans which is interpreted at 72 hr. The MIC was defined as the lowest drug concentration which showed a visual turbidity less than or equal to an 80 percent inhibition compared to that produced by the growth control tube.

Minimum Fungicidal Concentration (MFC) experiments were adapted from a method by McGinnis (McGinnis, M. R., (1980) "Susceptibility testing and bioassay procedure", p.431, Academic Press, Inc., New York). Briefly, 10 µl aliquots from tubes with growth inhibition were plated onto Sabouraud agar plates. The lowest drug concentration that yielded 3 or fewer yeasts colonies was recorded as the MFC. Several drugs were also rescreened with a subculture of 100 µl aliquots from tubes with no growth and there was no change in MFC.

Molds were tested by the National Committee for Clinical Laboratory Standards method cited above using the below-referenced modifications. Isolates were grown on Sabouraud dextrose agar at 30° C. and subcultured twice to insure viability. After adequate sporulation occurred (4–12 days), conidia were harvested by flooding colonies with a sterile solution of 0.85 percent NaCl and 0.05 percent Tween 80 in sterile distilled water. Inoculum suspensions were prepared using a hemocytometer for counting, then diluted with RPMI 1640 medium to obtain a final inoculum size of approximately $0.5-2.5\times10^3$ CFU/ml. The inoculum size was verified by plating an aliquot of the final concentration. Tests were incubated at 30° C. for 48–72 h or until growth in the control tube was visible. The reproducibility of the method was quality controlled by testing fluconazole and amphotericin B against C. albicans A39 and C. neoformans H99 in each experiment. MICs for fluconazole against C. albicans A39 and C. neoformansH99 were 0.25 µg/ml and 2 µµg/ml respectively. MICs for amphotericin B were 1 µg/ml against both isolates.

Tables 1–9 illustrate the antifungal activity according to the methods of the invention. As shown therein, the compounds used in the methods of the invention are effective in combating fungal infections, particularly in comparison to amphotericin, fluconazole, and pentamidine.

In the specification, and examples there have been disclosed typical preferred embodiments of the invention and, although specific terms are employed, they are used in a generic and descriptive sense only and not for the purposes of limitation, the scope of the invention being set forth in the following claims:

TABLE 1

Structure and in vitro activity of pentamidine analogs.

| | | | | | | Candida albicans | | Cryptococcus neoformans | |
|---|---|---|---|---|---|---|---|---|---|
| Compound | n | $Y^c$ | Position Y | X | R | $MIC_{80}^a$ (μg/ml) | $MFC^b$ (μg/ml) | $MIC_{80}^a$ (μg/ml) | $MFC^b$ (μ/ml) |
| Amphotericin | | | | | | 1.0 | $NT^d$ | 1.0 | $NT^d$ |
| Fluconazole | | | | | | 0.25 | $NA^e$ | 2.0 | $NA^e$ |
| Pentamidine | 5 | Am | 1 | O | H | 0.78 | 1.56 | 3.12 | 6.25 |
| 1 | 2 | Am | 1 | O | H | 3.12 | 100 | >100 | $NT^d$ |
| 2 | 2 | Am | 1 | O | $NH_2$ | 25 | $NT^d$ | >100 | $NT^d$ |
| 3 | 3 | Am | 1 | O | H | 3.12 | 3.12 | 6.25 | 6.25 |
| 4 | 3 | Am | 1 | O | $OCH_3$ | 12.5 | 50 | 12.5 | 12.5 |
| 5 | 3 | AmOH | 1 | O | H | >100 | $NT^d$ | >100 | $NT^d$ |
| 6 | 3 | AmOH | 1 | O | $OCH_3$ | >100 | $NT^d$ | >100 | $NT^d$ |
| 7 | 3 | Am | 2 | O | H | >100 | >100 | NT | $NT^d$ |
| 8 | 3 | Am | 1 | N | H | 0.19 | 0.39 | 1.56 | 6.25 |
| 9 | 3 | Am | 1 | N | $NH_2$ | 12.5 | >100 | 25 | 50 |
| 10 | 3 | Am | 1 | N | $NO_2$ | 100 | 100 | 100 | 100 |
| 11 | 4 | Am | 1 | O | H | 25 | 50 | 3.12 | 6.25 |
| 12 | 4 | Am | 1 | O | $OCH_3$ | >100 | >100 | 50 | >100 |
| 13 | 4 | Am | 1 | O | $NH_2$ | 6.25 | $NT^d$ | 12.5 | 50 |
| 14 | 4 | Im | 1 | O | H | 0.78 | 1.56 | 6.25 | 12.5 |
| 15 | 4 | $ImCH_3$ | 1 | O | H | >100 | >100 | >100 | >100 |
| 16 | 4 | Am | 2 | O | H | 12.5 | 25 | 25 | 25 |
| 17 | 5 | Am | 1 | O | Cl | 3.12 | 6.25 | 1.56 | 3.12 |
| 18 | 5 | Am | 1 | N | H | ≤0.09 | 0.39 | 0.78 | 1.56 |
| 19 | 6 | Am | 2 | O | H | 1.58 | 12.5 | 6.25 | 12.5 |
| 20 | 6 | Am | 1 | N | $NH_2$ | 0.78 | 3.12 | 0.78 | 3.12 |

[a]Minimum inhibitory concentration 80%.
[b]Minimum fungicidal concentration.

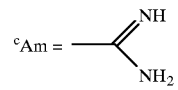

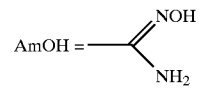

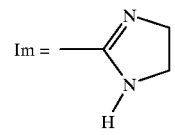

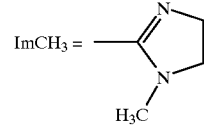

[d]Not tested.
[e]Not active.

TABLE 2

Structure and in vitro activity of pentamidine metabolites.

$$Y-\text{C}_6\text{H}_4-\text{O}-(CH_2)_2-\underset{R_5}{C}-(CH_2)_2-\text{O}-\text{C}_6\text{H}_4-Y$$

| | | | | | Candida albicans | | Cryptococcus neoformans | |
|---|---|---|---|---|---|---|---|---|
| Compound | Structure | $Y^c$ | R | Position R | $MIC_{80}{}^a$ (µg/ml) | $MFC^b$ (µg/ml) | $MIC_{80}{}^a$ (µg/ml) | $MFC^b$ (µg/ml) |
| Amphotericin | | | | | 1.0 | $NT^d$ | 1.0 | $NT^d$ |
| Fluconazole | | | | | 0.25 | $NA^e$ | 2.0 | $NA^e$ |
| Pentamidine | | Am | H | — | 0.78 | 1.56 | 3.12 | 6.25 |
| 21 | | Am | —OH | 2 | 6.25 | 12.5 | 6.25 | 12.5 |
| 22 | | Am | —OH | 3 | 12.5 | 12.5 | 12.5 | 12.5 |
| 23 | | AmOH | —H | — | >100 | $NT^d$ | >100 | $NT^d$ |

$^a$See footnotes Table I.

TABLE 3

Structure and in vitro activity of benzimidazole compounds.

| | | | Candida albicans | | Cryptococcus neoformans | |
|---|---|---|---|---|---|---|
| Cmpd | X | $Y^c$ | $MIC_{80}{}^a$ (µg/ml) | $MFC^b$ (µg/ml) | $MIC_{80}{}^a$ (µg/ml) | $MFC^b$ (µg/ml) |
| 28 | $(CH_2)_1$ | Am | >100 | $NT^d$ | >100 | $NT^d$ |
| 29 | $(CH_2)_1$ | Im | >100 | >100 | 100 | >100 |
| 30 | $(CH_2)_2$ | Am | 12.5 | 50 | 6.25 | 25 |
| 31 | $(CH_2)_2$ | Im | 100 | >100 | 25 | 50 |
| 32 | —C≡C— | Am | 6.25 | 12.5 | 1.56 | 3.12 |
| 33 | $(CH_2)_3$ | Am | >100 | >100 | >100 | $NT^d$ |
| 34 | $(CH_2)_4$ | Im | >100 | >100 | >100 | >100 |

| | | | Candida albicans | | Cryptococcus neoformans | |
|---|---|---|---|---|---|---|
| Cmpd | X | Y | $MIC_{80}{}^a$ (µg/ml) | $MFC^b$ (µg/ml) | $MIC_{80}{}^a$ (µg/ml) | $MFC^b$ (µg/ml) |
| 47 | –C₆H₄– | Am | >100 | $NT^d$ | 0.39 | 0.39 |
| 48 | –C₆H₄– | Im | 0.78 | 6.25 | 0.78 | 1.56 |
| 49 | –C₆H₄– | THP | 1.56 | 3.12 | 0.78 | 1.56 |

TABLE 3-continued
Structure and in vitro activity of benzimidazole compounds.
| | | | | | | |
|---|---|---|---|---|---|---|
| 50 | 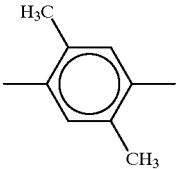 | Am | 25 | 100 | 25 | 25 |
| 53 | 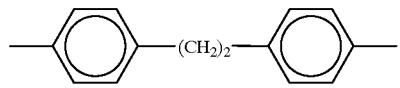 | IsopropAm | 1.56 | 6.25 | 0.39 | 0.78 |
| 54 | 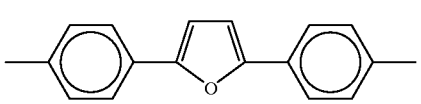 | CyclopentAm | 1.56 | 1.56 | 1.56 | 6.25 |
| 55 | 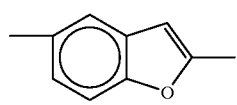 | Am | 0.39 | 0.78 | 0.19 | 0.19 |
| 56 | 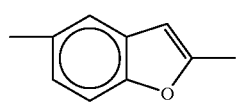 | CyclopentAm | 0.78 | 0.78 | 0.78 | 0.78 |
| 57 | 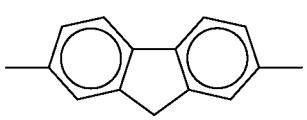 | IsopropAm | 0.78 | 1.56 | 0.78 | 0.78 |
[a]Minimum inhibitory concentration 80%.
[b]Minimum fungicidal concentration.
[c]Am = 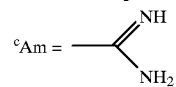
Im = 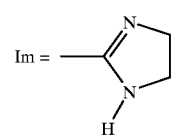
IsopropAm = 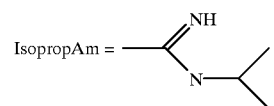
Cyclopent = 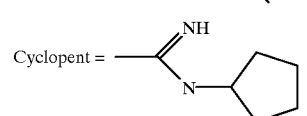
THP = 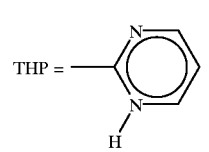
[d]Not tested.

TABLE 4

Structure and in vitro activity of para-substituted symmetrical furans.

| Compound | $Y_1$ | $Y_2{}^c$ | $R_1$ | $R_2$ | Candida albicans $MIC_{80}{}^a$ (µg/ml) | Candida albicans $MFC^b$ (µg/ml) | Cryptococcus neoformans $MIC_{80}{}^a$ (µg/ml) | Cryptococcus neoformans $MFC^b$ (µg/ml) |
|---|---|---|---|---|---|---|---|---|
| Amphotericin | | | | | 1.0 | $NT^d$ | 1.0 | $NT^d$ |
| Fluconazole | | | | | 0.25 | $NA^e$ | 2.0 | $NA^e$ |
| 16 | NH | $NH_2$ | H | H | 6.25 | 25 | 12.5 | 25 |
| 17 | NH | $NH_2$ | $CH_3$ | $CH_3$ | 6.25 | 6.25 | 3.12 | 3.12 |
| 18 | $NOCH_3$ | $NH_2$ | H | H | >100 | $NT^d$ | >100 | $NT^d$ |
| 19 | NH | NH-cPr | H | H | 25 | 25 | 3.12 | 50 |
| 20 | NH | NH-cBt | H | H | 6.25 | >50 | 0.78 | 6.25 |
| 21 | NH | NH-cPt | H | H | 6.25 | 25 | 0.78 | 6.25 |
| 22 | NH | NH-cHx | H | H | 12.5 | 12.5 | 1.56 | 6.25 |
| 23 | NH | NH—$CH_2$-cPr | H | H | 6.25 | 25 | 0.78 | 6.25 |
| 24 | NH | NH—$(CH_2)_2CH_3$ | H | H | 12.5 | 12.5 | 1.56 | 6.25 |
| 25 | NH | NH—$CH(CH_3)_2$ | H | H | 25 | 50 | 6.25 | 50 |
| 26 | NH | NH—$CH(CH_2CH_3)_2$ | H | H | 100 | 100 | 12.5 | 12.5 |
| 27 | NH | NH—$CH_2$—$CH(CH_3)_2$ | H | H | 12.5 | $NT^d$ | 3.12 | 12.5 |
| 28 | NH | NH—$(CH_2)_2$—$CH(CH_3)_2$ | H | H | 12.5 | 12.5 | 6.25 | 12.5 |
| 29 | NH | NH—$(CH_2)^3$—Pyr | H | H | >100 | $NT^d$ | 6.25 | 25 |
| 30 | NH | NH—$(CH_2)_3$PipCH$_3$ | H | H | >100 | $NT^d$ | 12.5 | 50 |
| 31 | NH | NH—$(CH_2)_4$—$NH(CH_3)_2$ | H | H | 12.5 | 25 | ≦0.09 | 0.19 |
| 32 | NH | NH—$(CH_2)_6$—$NH(CH_3)_2$ | H | H | >100 | $NT^d$ | 1.56 | 3.12 |
| 33 | O | NH—$(CH_2)_3$Oxz | H | H | >100 | $NT^d$ | >100 | $NT^d$ |
| 34 | O | NH—$(CH_2)_2$—$NH(CH_3)_2$ | H | H | >100 | $NT^d$ | >100 | $NT^d$ |
| 35 | O | NH—$(CH_2)_3$—$NH(CH_3)_2$ | H | H | >100 | $NT^d$ | >100 | $NT^d$ |
| 36 | O | NH—$(CH_2)_3$—$NHCH_3Ph$ | H | H | >100 | $NT^d$ | >100 | $NT^d$ |
| 37 | O | $NCH_3$—$(CH_2)_3$—$NH(CH_3)_2$ | H | H | >100 | $NT^d$ | >110 | $NT^d$ |

[a]Minimum inhibitory concentration 80%.
[b]Minimum fungicidal concentration.

cPr = 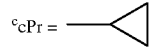

cBt = 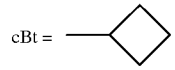

cPt = 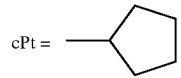

cHx = 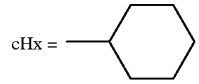

Pip = 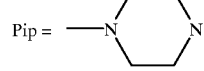

Oxz = 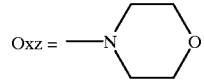

Pyr = 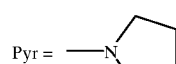

Ph = 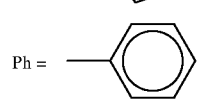

[d]Not tested.
[e]No activity.

TABLE 5

Structure and in vitro activity of meta-substituted symmetrical furans.

| | | Candida albicans | | Cryptococcus neoformans | |
|---|---|---|---|---|---|
| Compound | Y | MIC$_{80}$[a] (μg/ml) | MFC[b] (μg/ml) | MIC$_{80}$[a] (μg/ml) | MFC[b] (μg/ml) |
| Amphotericin | | 1.0 | NT[c] | 1.0 | NT[c] |
| Fluconazole | | 0.25 | NA[d] | 2.0 | NA[d] |
| 38 | —C(=NH)NH$_2$ | 50 | 100 | 3.12 | 25 |
| 39 | 2-imidazoline | 50 | 100 | 12.5 | 25 |
| 40 | —C(=NH)NH—CH(CH$_3$)$_2$ | 100 | >100 | 6.25 | 6.25 |
| 41 | —C(=NH)NH—(CH$_2$)$_2$—N(CH$_3$)$_2$ | >100 | NT[c] | 12.5 | 50 |
| 42 | —C(=NH)NH—(CH$_2$)$_3$—N(CH$_3$)$_2$ | >100 | NT[c] | 25 | >100 |

[a]Minimum inhibitory concentration 80%.
[b]Minimum fungicidal concentration.
[c]Not tested.
[d]No activity.

TABLE 6

Structure and in vitro activity of asymmetrical furans.

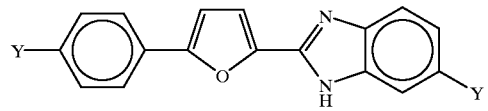

| | | Candida albicans | | Cryptococcus neoformans | |
|---|---|---|---|---|---|
| Compound | Y | MIC$_{80}$[a] (μg/ml) | MFC[b] (μg/ml) | MIC$_{80}$[a] (μg/ml) | MFC[b] (μg/ml) |
| Amphotericin | | 1.0 | NT[c] | 1.0 | NT[c] |
| Fluconazole | | 0.25 | NA[d] | 2.0 | NA[d] |

TABLE 6-continued

Structure and in vitro activity of asymmetrical furans.

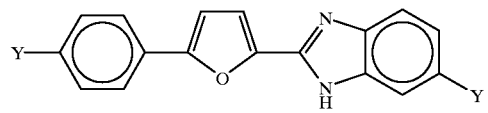

| Compound | Y | Candida albicans MIC$_{80}$[a] (μg/ml) | Candida albicans MFC[b] (μg/ml) | Cryptococcus neoformans MIC$_{80}$[a] (μg/ml) | Cryptococcus neoformans MFC[b] (μg/ml) |
|---|---|---|---|---|---|
| 43 | =NH, NH$_2$ | 3.12 | 3.12 | 3.12 | 3.12 |
| 44 | =NH, NH-CH(CH$_3$)$_2$ | >100 | NT[c] | 12.5 | 100 |
| 45 | 2-methylimidazoline | 3.12 | 50 | 1.56 | 6.25 |
| 46 | =NH, NH-cyclopentyl | >100 | NT[c] | 12.5 | 25 |
| 47 | =NH, NH-(CH$_2$)$_3$-N(CH$_3$)$_2$ | >100 | NT[c] | 6.25 | 25 |

[a]Minimum inhibitory concentration 80%.
[b]Minimum fungicidal concentration.
[c]Not tested.
[d]No activity.

TABLE 7

Structure and in vitro activity of benzimidazoles.

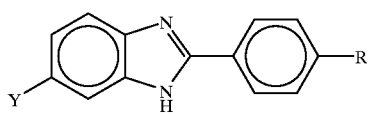

| Compound | Y[c] | R[c] | Candida albicans MIC$_{80}$[a] (μg/ml) | Candida albicans MFC[b] (μg/ml) | Cryptococcus neoformans MIC$_{80}$[a] (μg/ml) | Cryptococcus neoformans MFC[b] (μg/ml) |
|---|---|---|---|---|---|---|
| Amphotericin | | | 1.0 | NT[d] | 1.0 | NT[d] |
| Fluconazole | | | 0.25 | NA[e] | 2.0 | NA[e] |
| 48 | BzIm | OH | 3.12 | NT[d] | 3.12 | NT[d] |
| 49 | BzIm | OCH$_3$ | 0.78 | NT[d] | 3.12 | 3.12 |
| 50 | BzIm | OC$_2$H$_5$ | 0.78 | 12.5 | 1.56 | 1.56 |
| 51 | BzTHP | OH | 3.12 | 25 | 1.56 | 6.25 |
| 52 | BzAm | OH | 0.78 | 6.25 | 3.12 | 6.25 |
| 53 | BzAm | Am | 0.39 | 1.56 | ≦0.09 | 0.78 |
| 54 | BzIm | Im | 0.78 | 1.56 | 0.39 | 0.39 |

TABLE 7-continued

Structure and in vitro activity of benzimidazoles.

| Compound | Y[c] | R[c] | Candida albicans MIC$_{80}$[a] (μg/ml) | MFC[b] (μg/ml) | Cryptococcus neoformans MIC$_{80}$[a] (μg/ml) | MFC[b] (μg/ml) |
|---|---|---|---|---|---|---|
| 55 | BzAm | OCH$_3$ | >100 | NT[d] | 3.12 | >25 |
| 56 | BzTHP | THP | 0.78 | 1.56 | 0.19 | 0.39 |
| 57 | BzAm | OC$_2$H$_5$ | 0.78 | 1.56 | 1.56 | 1.56 |
| 58 | BzMPZ | OH | 25 | 50 | 100 | >100 |
| 59 | Im | OCH$_3$ | 25 | NT[d] | 50 | 100 |
| 60 | Am | Am | 100 | >100 | 25 | 50 |
| 61 | Am | OH | >100 | NT[d] | >100 | >100 |
| 62 | Im | Im | 50 | >100 | 50 | NT[d] |
| 63 | THP | THP | 50 | 100 | 25 | 50 |
| 64 | Am | O(CH$_2$)$_3$OPhAm | 0.39 | 0.78 | 0.19 | 0.78 |
| 65 | Am | O(CH$_2$)$_4$OPhAm | 0.39 | 3.12 | ≦0.09 | 1.56 |
| 66 | Am | O(CH$_2$)$_5$OPhAm | 0.78 | 1.56 | 0.39 | 6.25 |
| 67 | Am | OPhAm | 0.78 | 0.78 | 0.78 | 6.25 |

[a]Minimum inhibitory concentration 80%.
[b]Minimum fungicidal concentration.

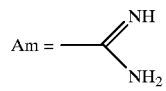

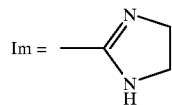

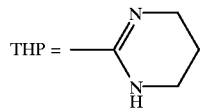

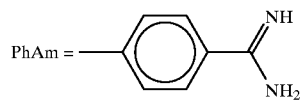

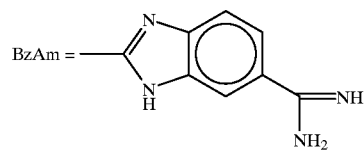

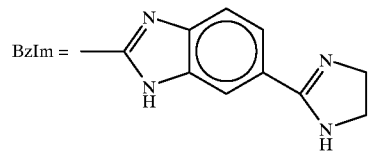

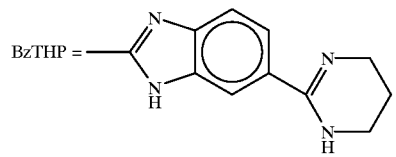

TABLE 7-continued

Structure and in vitro activity of benzimidazoles.

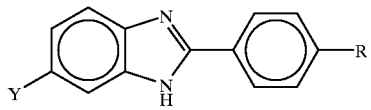

| Compound | $Y^c$ | $R^c$ | Candida albicans $MIC_{80}^a$ (μg/ml) | $MFC^b$ (μg/ml) | Cryptococcus neoformans $MIC_{80}^a$ (μg/ml) | $MFC^b$ (μg/ml) |
|---|---|---|---|---|---|---|
| BzMPZ = | | | | | | |

[structure of BzMPZ: benzimidazole with N-methylpiperazine substituent]

[d] Not tested.
[e] No activity.

TABLE 8

Extended antifungal spectrum of selected compounds.

| | Compound 39 | | Compound 57 | |
|---|---|---|---|---|
| Strains | $MIC_{80}^a$ (μg/ml) | $MFC^b$ (μg/ml) | $MIC_{80}^a$ (μg/ml) | $MFC^b$ (μg/ml) |
| Candida albicans A39 | 0.78 | 0.78 | 0.78 | 1.56 |
| C. albicans 102.96[c] | 0.39 | 0.78 | 1.56 | 12.5 |
| C. albicans 103.96[c] | 0.78 | 0.78 | 1.56 | 12.5 |
| C. krusei 132.91[c] | $NT^d$ | $NT^d$ | 0.78 | 0.78 |
| C. lusitaniae 111.92 | $NT^d$ | $NT^d$ | 0.78 | 3.12 |
| C. parapsilosis 111.96 | $NT^d$ | $NT^d$ | 0.78 | 0.78 |
| C. tropicalis 110.96 | $NT^d$ | $NT^d$ | 0.78 | 1.56 |
| Torulopsis glabrata 142.91 | $NT^d$ | $NT^d$ | 0.78 | 0.78 |
| Cryptococcus neoformans H99 | 0.78 | 0.78 | 0.78 | 0.78 |
| C. neoformans 114.96[c] | $NT^d$ | $NT^d$ | 0.78 | 0.78 |
| Aspergillus flavus 112.96 | >100 | $NT^d$ | $NT^d$ | $NT^d$ |
| A. fumigatus 168.95 | 0.19 | 3.12 | $NT^d$ | $NT^d$ |
| Fusarium solani 152.89 | 0.39 | 0.39 | $NT^d$ | $NT^d$ |

[a] Minimum inhibitory concentration 80%.
[b] Minimum fungicidal concentration.
[c] Fluconazole-resistant isolates.
[d] Not tested.

TABLE 9

Extended antifungal spectrum of selected compounds.

| | Compound 10 | | Compound 21 | | Compound 53 | |
|---|---|---|---|---|---|---|
| Strains | $MIC_{80}^a$ (μg/ml) | $MFC^b$ (μg/ml) | $MIC_{80}^a$ (μg/ml) | $MFC^b$ (μg/ml) | $MIC_{80}^a$ (μg/ml) | $MFC^b$ (μg/ml) |
| Candida albicans A39 | 0.78 | 1.56 | 6.25 | 25 | 0.39 | 1.56 |
| C. albicans 102.96[c] | $NT^d$ | $NT^d$ | 12.5 | 12.5 | $NT^d$ | $NT^d$ |
| C. albicans 103.96[c] | $NT^d$ | $NT^d$ | 12.5 | 12.5 | $NT^d$ | $NT^d$ |
| C. krusei 132.91 | 1.56 | 12.5 | 12.5 | >100 | 0.39 | 0.39 |
| C. lusitaniae 111.92 | 3.12 | 25 | 6.25 | 25 | 0.39 | 1.56 |
| C. parapsilosis 111.96 | 0.78 | >6.25 | 6.25 | 100 | 0.39 | 0.39 |
| C. tropicalis 110.96 | ≦0.09 | 0.19 | 3.12 | 12.5 | 0.39 | 0.39 |
| Torulopsis glabrata 142.91 | 0.78 | >12.5 | 0.78 | >6.25 | ≦0.09 | 0.78 |
| Cryptococcus neoformans H99 | 6.25 | >50 | 0.39 | 6.25 | <0.09 | 0.78 |
| C. neoformans 114.95[e] | 6.25 | 12.5 | 0.78 | 3.12 | 0.19 | 0.39 |
| C. neoformans 119.95[f] | 1.56 | 6.25 | 0.39 | 1.56 | 0.19 | 0.39 |
| C. neoformans 133.95[c] | $NT^d$ | $NT^d$ | 0.39 | 1.56 | $NT^d$ | $NT^d$ |
| C. neoformans 135.95[c] | 3.12 | 6.25 | 0.39 | 1.56 | ≦0.09 | 0.19 |
| C. neoformans 167.95 | $NT^d$ | $NT^d$ | 0.39 | 0.78 | $NT^d$ | $NT^d$ |

TABLE 9-continued

| | Extended antifungal spectrum of selected compounds. | | | | | |
|---|---|---|---|---|---|---|
| | Compound 10 | | Compound 21 | | Compound 53 | |
| Strains | $MIC_{80}{}^a$ (µg/ml) | $MFC^b$ (µg/ml) | $MIC_{80}{}^a$ (µg/ml) | $MFC^b$ (µg/ml) | $MIC_{80}{}^a$ (µg/ml) | $MFC^b$ (µg/ml) |
| *C. neoformans* 114.96[c] | 6.25 | 25 | 0.78 | 1.56 | ≦0.09 | 0.19 |
| *Aspergillus flavus* 112.96 | 50 | 50 | 25 | $NT^d$ | >100 | $NT^d$ |
| *A. fumigatus* 168.95 | 3.12 | 25 | 1.56 | $NT^d$ | ≦0.09 | $NT^d$ |
| *Fusarium solani* 152.89 | 50 | 100 | >100 | $NT^d$ | 0.19 | $NT^d$ |
| *Paecilomyces lilacinus* 137.90 | 100 | $NT^d$ | >100 | $NT^d$ | >100 | $NT^d$ |
| *Rhizopus arrhizus* 117.89 | 25 | 50 | 25 | $NT^d$ | >100 | $NT^d$ |

[a] Minimum inhibitory concentration 80%.
[b] Minimum fungicidal concentration.
[c] Fluconazole-resistant isolates.
[d] Not tested.
[e] Serotype B.
[f] Serotype C.

That which is claimed:

1. A method of combating a fungal infection selected from the group consisting of *Candida albicans, Cryptococcus neoformans, Aspergillus fumigatus,* and *Fusarium solani* in a subject in need of such treatment, comprising administering to the subject an effective fungal infection-combating amount of a compound [(I)–(II)] selected from the group consisting of:

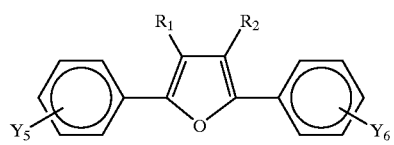
(I)

wherein $R_1$ and $R_2$ may be the same or different and selected from the group consisting of H, loweralkyl, aryl, alkylaryl, aminoalkyl, aminoaryl, halogen, oxyalkyl, oxyaryl, and oxyarylalkyl; and wherein $Y_5$ and $Y_6$ are present in the meta or para positions and may the same or different and are represented by the formula (a) or (b) selected from the group consisting of:

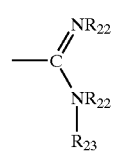
(a)

wherein:

each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; and

(b)

wherein $Y_3$ is selected from the group consisting of NR''' and O;

wherein R''' is selected from the group consisting of H and loweralkyl;

and wherein $Y_4$ is represented by the formula:

$$\begin{array}{c} NR_{20} \\ | \\ R_{21} \end{array}$$

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl;

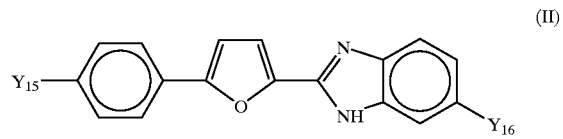
(II)

wherein $Y_{15}$ and $Y_{16}$ may be the same or different and represented by the formula:

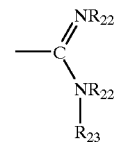

wherein:

each $R_{22}$ is independently selected from the group consisting of H, loweralkyl, alkoxyalkyl, hydroxyalkyl, aminoalkyl, alkylaminoalkyl, alkylamino, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

2. The method according to claim 1, wherein said compound is represented by the formula:

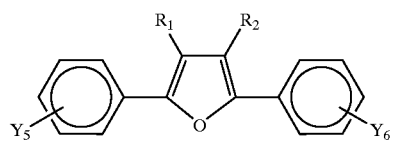

(I)

wherein $R_1$ and $R_2$ may be the same or different and selected from the group consisting of H, loweralkyl, aryl, alkylaryl, aminoalkyl, aminoaryl, halogen, oxyalkyl, oxyaryl, and oxyarylalkyl; and wherein $Y_5$ and $Y_6$ are present in the meta or para positions and may the same or different and are represented by the formula (a) or (b) selected from the group consisting of:

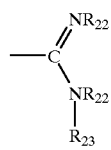

(a)

wherein:

each $R_{22}$ is independently selected from the group consisting of H, loweralkyl, alkoxyalkyl, hydroxyalkyl, aminoalkyl, alkylaminoalkyl, alkylaminoalkyl, cycloalkyl, aryl, or alkylaryl or two $R_{22}$ groups together represent $C_2$–$C_{10}$ alkyl, hydroxyalkyl, or alkylene; or $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; and

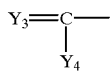

(b)

wherein $Y_3$ is selected from the group consisting of NR'" and O;

wherein R'" is selected from the group consisting of H and loweralkyl;

and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl.

3. The method according to claim 1, wherein said compound is represented by the formula:

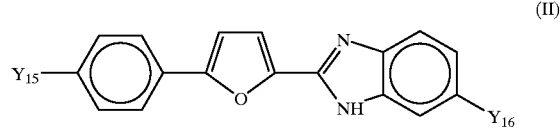

(II)

wherein $Y_{15}$ and $Y_{16}$ may be the same or different and represented by the formula:

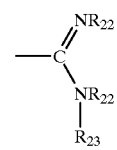

wherein:

each $R_{22}$ is independently selected from the group consisting of H, loweralkyl, alkoxyalkyl, hydroxyalkyl, aminoalkyl, alkylaminoalkyl, alkylamino, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, and alkylaminoalkyl, cycloalkyl, hydroxcycloalkyl, alkoxycycloalkyl, aryl, or alkylaryl.

4. The method according to claim 1, wherein said method comprises administering a compound of formula (I) to said subject and wherein $Y_5$ and Y6 are each independently represented by the formula:

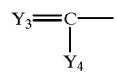

wherein $Y_3$ is selected from the group consisting of NR'" and O;

wherein R'" is selected from the group consisting of H, $OCH_3$, and loweralkyl;

and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl.

5. The method according to claim 4, wherein $R_1$ and $R_2$ are each hydrogen.

6. The method according to claim 4, wherein $Y_3$ is NH and $Y_4$ is selected from the group consisting of $NH_2$,

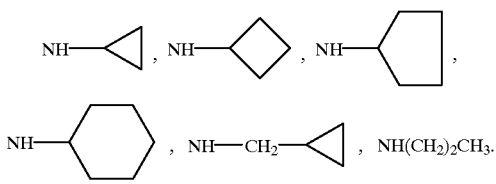

7. The method according to claim 4, wherein $Y_3$ is $NOCH_3$ and $Y_4$ is $NH_2$.

8. The method according to claim 4, wherein $R_1$ and $R_2$ are each $CH_3$, $Y_3$ is $NOCH_3$ and $Y_4$ is $NH_2$.

9. The method according to claim 1, wherein said method comprises administering a compound of formula (II) to said subject.

10. The method according to claim 9, wherein $Y_{15}$ and $Y_{16}$ are the same and are each represented by the formula:

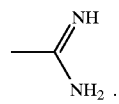

11. The method according to claim 9, wherein $Y_{15}$ and $Y_{16}$ are the same and are each represented by the formula:

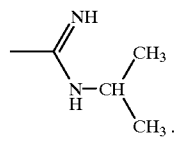

12. The method according to claim 9, wherein $Y_{15}$ and $Y_{16}$ are the same and are each represented by the formula:

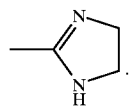

13. The method according to claim 9, wherein $Y_{15}$ and $Y_{16}$ are the same and are each represented by the formula:

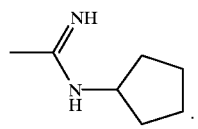

14. The method according to claim 9, wherein $Y_{15}$ and $Y_{16}$ are the same and are each represented by the formula:

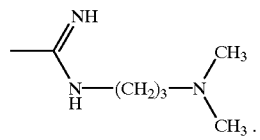

15. A method of combating a fungal infection selected from the group consisting of *Candida albicans* and *Cryptococcus neoformans* in a subject in need of such treatment, comprising administering to said subject an effective fungal infection-combating amount of a compound (I)–(II) selected from the group consisting of:

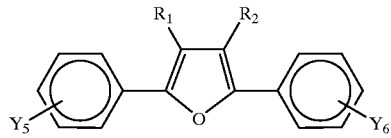

(I)

wherein $R_1$ and $R_2$ may be the same or different and selected from the group consisting of H, loweralkyl, aryl, alkylaryl, aminoalkyl, aminoaryl, halogen, oxyalkyl, oxyaryl, and oxyarylalkyl; and wherein $Y_5$ and $Y_6$ are present in the meta or para positions and may the same or different and are represented by the formula (a) or (b) selected from the group consisting of:

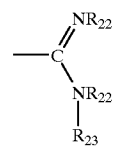

(a)

wherein:

each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; and

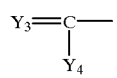

(b)

wherein $Y_3$ is selected from the group consisting of NR''' and O;

wherein R''' is selected from the group consisting of H and loweralkyl;

and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl; and (II)

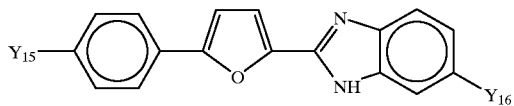

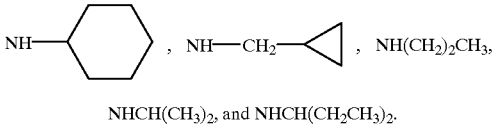

wherein $Y_{15}$ and $Y_{16}$ may be the same or different and represented by the formula:

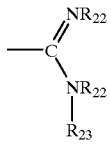

wherein:

each $R_{22}$ is independently selected from the group consisting of H, loweralkyl, alkylamino, alkoxyalkyl, hydroxyalkyl, aminoalkyl, alkylaminoalkyl, cycloalkyl, aryl, or alkylaryl or two $R_{22}$ groups together represent $C_2$–$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

16. The method according to claim 15, wherein said method comprises administering a compound of formula (I) to said subject and wherein $Y_5$ and $Y_6$ are each independently represented by the formula:

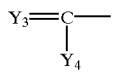

wherein $Y_3$ is selected from the group consisting of NR''' and O;

wherein R''' is selected from the group consisting of H, $OCH_3$, and loweralkyl;

and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl;

wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl.

17. The method according to claim 16, wherein $R_1$ and $R_2$ are each hydrogen.

18. The method according to claim 17, wherein $Y_3$ is NH and $Y_4$ is selected from the group consisting of $NH_2$,

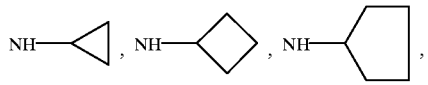

19. The method according to claim 17, wherein $Y_3$ is $NOCH_3$ and $Y_4$ is $NH_2$.

20. The method according to claim 16, wherein $R_1$ and $R_2$ are each $CH_3$, $Y_3$ is $NOCH_3$ and $Y_4$ is $NH_2$.

21. The method according to claim 15, wherein said method comprises administering a compound of formula (II) to said subject.

22. The method according to claim 21, wherein $Y_{15}$ and $Y_{16}$ are the same and are each represented by the formula:

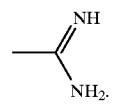

23. The method according to claim 21, wherein $Y_{15}$ and $Y_{16}$ are the same and are each represented by the formula:

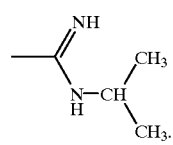

24. The method according to claim 21, wherein $Y_{15}$ and $Y_{16}$ are the same and are each represented by the formula:

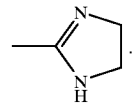

25. The method according to claim 21, wherein $Y_{15}$ and $Y_{16}$ are the same and are each represented by the formula:

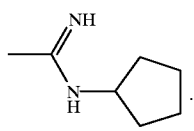

26. The method according to claim 21, wherein $Y_{15}$ and $Y_{16}$ are the same and are each represented by the formula:

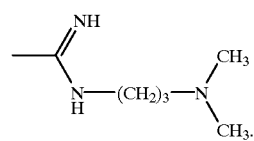

27. A compound for administering to a subject in need of fungal treatment represented by the formula:

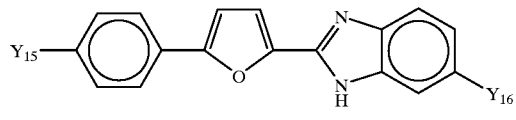

wherein $Y_{15}$ and $Y_{16}$ may be the same or different and represented by the formula:

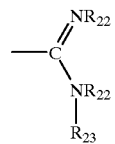

wherein each $R_{22}$ is independently selected from the group consisting of H, loweralkyl, alkoxyalkyl, hydroxyalkyl, aminoalkyl, alkylamino, alkylaminoalkyl, cycloalkyl, aryl, or alkylaryl or two $R_{22}$ groups together represent $C_2$–$C_{10}$ alkyl, hydroxyalkyl, or alkylene;

$R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl;

and pharmaceutically acceptable salts thereof.

28. A pharmaceutical composition comprising a therapeutically effective amount of a compound in claim 27 in a pharmaceutically acceptable carrier.

* * * * *